(12) United States Patent
Fortman et al.

(10) Patent No.: US 9,334,514 B2
(45) Date of Patent: May 10, 2016

(54) HYBRID POLYKETIDE SYNTHASES

(75) Inventors: Jeffrey L. Fortman, San Francisco, CA (US); Andrew Hagen, Berkeley, CA (US); Leonard Katz, Oakland, CA (US); Jay D. Keasling, Berkeley, CA (US); Sean Poust, Berkeley, CA (US); Jingwei Zhang, San Francisco, CA (US); Sergey Zotchev, Trondheim (NO)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/882,099

(22) PCT Filed: Oct. 31, 2011

(86) PCT No.: PCT/US2011/058660
§ 371 (c)(1),
(2), (4) Date: Jul. 10, 2013

(87) PCT Pub. No.: WO2012/058686
PCT Pub. Date: May 3, 2012

(65) Prior Publication Data
US 2013/0280766 A1    Oct. 24, 2013

Related U.S. Application Data

(60) Provisional application No. 61/408,411, filed on Oct. 29, 2010.

(51) Int. Cl.
| | |
|---|---|
| *C12P 17/18* | (2006.01) |
| *C12P 7/44* | (2006.01) |
| *C12P 7/46* | (2006.01) |
| *C12P 13/00* | (2006.01) |
| *C12P 13/04* | (2006.01) |

(Continued)

(52) U.S. Cl.
CPC ........... *C12P 17/186* (2013.01); *C12N 15/52* (2013.01); *C12P 7/44* (2013.01); *C12P 7/46* (2013.01); *C12P 13/001* (2013.01); *C12P 13/005* (2013.01); *C12P 13/04* (2013.01); *C12P 17/10* (2013.01)

(58) Field of Classification Search
None
See application file for complete search history.

(56) References Cited

U.S. PATENT DOCUMENTS

| | | | | |
|---|---|---|---|---|
| 8,569,023 | B2 * | 10/2013 | Katz et al. | 435/142 |
| 2013/0267012 | A1 * | 10/2013 | Steen et al. | 435/254.21 |

FOREIGN PATENT DOCUMENTS

| | | | |
|---|---|---|---|
| WO | WO 2009/113853 A2 | | 9/2009 |
| WO | WO 2009/121066 | * | 10/2009 |
| WO | WO 2009/121066 A1 | | 10/2009 |

OTHER PUBLICATIONS

Holtzel et al., Spirofungin, a New Antifungal Antibiotic from *Streptomyces violaceusniger* Tü 4113, The Journal of Antibiotics (1998), vol. 51, No. 8, pp. 699-707.*

(Continued)

*Primary Examiner* — Alexander Kim
(74) *Attorney, Agent, or Firm* — Kilpatrick Townsend & Stockton LLP

(57) ABSTRACT

The present invention provides for a polyketide synthase (PKS) capable of synthesizing an even-chain or odd-chain diacid or lactam or diamine. The present invention also provides for a host cell comprising the PKS and when cultured produces the even-chain diacid, odd-chain diacid, or KAPA. The present invention also provides for a host cell comprising the PKS capable of synthesizing a pimelic acid or KAPA, and when cultured produces biotin.

17 Claims, 20 Drawing Sheets adipic acid

(51) Int. Cl.
*C12N 15/52* (2006.01)
*C12P 17/10* (2006.01)

(56) References Cited

OTHER PUBLICATIONS

International Search Report from PCT/US2011/058660, dated May 25, 2012.
Ansari et al.; "NRPS-PKS: a knowledge-based resource for analysis of NRPS/PKS megasynthases"; *Nucl. Acids Res.*; 32(Web Server issue):W405-413 (Jul. 1, 2004).
Brautaset et al.; "Biosynthesis of the polyene antifungal antibiotic nystatin in *Streptomyces noursei* ATCC 11455: analysis of the gene cluster and deduction of the biosynthetic pathway"; *Chem. Biol.*; 7(6):395-403 (2000).
Challis et al.; "Mining microbial genomes for new natural products and biosynthetic pathways"; *Microbiology*; 154(6):1555-1569 (2008).
Challis et al.; "Predictive, structure-based model fo amino acid recognition by nonribosomal peptide synthetase adenylation domains"; *Chem. Biol.*; 7(3):2111-224 (2000).
Dutton et al.; "Novel avermectins produced by mutational biosynthesis"; *J. Antibiot.* (Tokyo); 44(3):357-365 (1991).
Finking et al.; "Biosynthesis of nonribosomal peptides"; *Annu. Rev. Microbiol.*; 58:453-488 (2004).
Jez et al.; "Expanding the biosynthetic repertoire of plant type III polyketide synthases by altering starter molecule specificity"; *Proc. Natl. Acad. Sci. USA*; 99(8):5319-5324 (2002).
Khosla et al.; "Tolerance and specificity of polyketide synthases"; *Ann. Rev. Biochem.*; 68:219-253 (1999).
Li et al.; "Automated genome mining for natural products"; *BMC Bioinformatics*; 10(185):1-10 (2009).
Marsden et al.; "Engineering broader specificity into an antibiotic-producing polyketide synthase"; *Science*; 279(5348):199-202 (1998).
May et al.; "Crystal structure of DhbE, an archetype for aryl acid activating domains of modular nonribosomal peptide synthases"; *Proc. Natl. Acad. Sci. USA*; 99(19):12120-12125 (2002).
Menche et al.; "Stereochemical determination and complex biosynthetic assembly of etnangien, a highly potent RNA polymerase inhibitor from the myxobacterium *Sorangium cellulosum*"; *J. Am. Chem. Soc.*; 130(43):14234-14243 (2008).
Oliynyk et al.; "Complete genome sequence of the erythromycin-producing bacterium *Saccharopolyspora erythraea*NRRL233338"; *Nat. Biotechnol.*; 25(4):447-453 (2007).
Rachid et al.; "Unusual chemistry in the biosynthesis of the antibiotic chondrochlorens"; *Chem. Biol.*; 16(1):70-81 (2009).
Reeves et al.; "Alteration of the substrate specificity of modular polyketide synthase acyltransferase domain through site-specific mutations"; *Biochemistry*; 40(51):15464-15470 (2001).
Staunton et al.; "Polyketide biosynthesis: a millenium review"; *Nat. Prod. Rep.*; 18(4):380-416 (2001) ePub Jun. 4, 2001.
Wiesmann et al.; "Polyketide synthesis in vitro on a modular polyketide synthase"; *Chem. Biol.*; 2(9):583-589 (1995).

\* cited by examiner 2-methylhexanoic acid

Domain Function
1    CoA Binding
2    CoA ligase
3    ATP grasp
4    ATP grasp
5    CoA ligase

A.

2-Methylhexanedioic acid

B.

Adipic acid

II.1.ii.b. Design 2.

SEQUENCE LISTING

<160> NUMBER OF SEQ ID NOS: 5

<210> SEQ ID NO 1
<211> LENGTH: 244
<212> TYPE: PRT
<213> ORGANISM: Bacillus subtilis
<220> FEATURE:
<223> OTHER INFORMATION: pimelyl-CoA synthetase, bioW gene product

<400> SEQUENCE: 1

```
Met Asn Gly Ser His Glu Asp Gly Gly Lys His Ile Ser Gly Gly Glu
1               5                   10                  15

Arg Leu Ile Pro Phe His Glu Met Lys His Thr Val Asn Ala Leu Leu
            20                  25                  30

Glu Lys Gly Leu Ser His Ser Arg Gly Lys Pro Asp Phe Met Gln Ile
        35                  40                  45

Gln Phe Glu Glu Val His Glu Ser Ile Lys Thr Ile Gln Pro Leu Pro
    50                  55                  60

Val His Thr Asn Glu Val Ser Cys Pro Glu Glu Gly Gln Lys Leu Ala
65                  70                  75                  80

Arg Leu Leu Leu Glu Lys Glu Gly Val Ser Arg Asp Val Ile Glu Lys
                85                  90                  95

Ala Tyr Glu Gln Ile Pro Glu Trp Ser Asp Val Arg Gly Ala Val Leu
            100                 105                 110

Phe Asp Ile His Thr Gly Lys Arg Met Asp Gln Thr Lys Glu Lys Gly
        115                 120                 125

Val Arg Val Ser Arg Met Asp Trp Pro Asp Ala Asn Phe Glu Lys Trp
    130                 135                 140

Ala Leu His Ser His Val Pro Ala His Ser Arg Ile Lys Glu Ala Leu
145                 150                 155                 160

Ala Leu Ala Ser Lys Val Ser Arg His Pro Ala Val Val Ala Glu Leu
                165                 170                 175

Cys Trp Ser Asp Asp Pro Asp Tyr Ile Thr Gly Tyr Val Ala Gly Lys
            180                 185                 190

Lys Met Gly Tyr Gln Arg Ile Thr Ala Met Lys Glu Tyr Gly Thr Glu
```

```
                195                 200                 205
Glu Gly Cys Arg Val Phe Phe Ile Asp Gly Ser Asn Asp Val Asn Thr
            210                 215                 220

Tyr Ile His Asp Leu Glu Lys Gln Pro Ile Leu Ile Glu Trp Glu Glu
225                 230                 235                 240

Asp His Asp Ser

<210> SEQ ID NO 2
<211> LENGTH: 384
<212> TYPE: PRT
<213> ORGANISM: Escherichia coli
<220> FEATURE:
<223> OTHER INFORMATION: E. coli strain K-12, substrain W3110
      8-amino-7-oxononanoate synthase, bioF gene product

<400> SEQUENCE: 2

Met Ser Trp Gln Glu Lys Ile Asn Ala Ala Leu Asp Ala Arg Arg Ala
1               5                   10                  15

Ala Asp Ala Leu Arg Arg Arg Tyr Pro Val Ala Gln Gly Ala Gly Arg
            20                  25                  30

Trp Leu Val Ala Asp Asp Arg Gln Tyr Leu Asn Phe Ser Ser Asn Asp
        35                  40                  45

Tyr Leu Gly Leu Ser His His Pro Gln Ile Ile Arg Ala Trp Gln Gln
    50                  55                  60

Gly Ala Glu Gln Phe Gly Ile Gly Ser Gly Gly Ser Gly His Val Ser
65                  70                  75                  80

Gly Tyr Ser Val Val His Gln Ala Leu Glu Glu Glu Leu Ala Glu Trp
                85                  90                  95

Leu Gly Tyr Ser Arg Ala Leu Leu Phe Ile Ser Gly Phe Ala Ala Asn
            100                 105                 110

Gln Ala Val Ile Ala Ala Met Met Ala Lys Glu Asp Arg Ile Ala Ala
        115                 120                 125

Asp Arg Leu Ser His Ala Ser Leu Leu Glu Ala Ala Ser Leu Ser Pro
    130                 135                 140

Ser Gln Leu Arg Arg Phe Ala His Asn Asp Val Thr His Leu Ala Arg
145                 150                 155                 160

Leu Leu Ala Ser Pro Cys Pro Gly Gln Gln Met Val Val Thr Glu Gly
                165                 170                 175

Val Phe Ser Met Asp Gly Asp Ser Ala Pro Leu Ala Glu Ile Gln Gln
            180                 185                 190

Val Thr Gln Gln His Asn Gly Trp Leu Met Val Asp Asp Ala His Gly
        195                 200                 205

Thr Gly Val Ile Gly Glu Gln Gly Arg Gly Ser Cys Trp Leu Gln Lys
    210                 215                 220

Val Lys Pro Glu Leu Leu Val Val Thr Phe Gly Lys Gly Phe Gly Val
225                 230                 235                 240

Ser Gly Ala Ala Val Leu Cys Ser Ser Thr Val Ala Asp Tyr Leu Leu
                245                 250                 255

Gln Phe Ala Arg His Leu Ile Tyr Ser Thr Ser Met Pro Pro Ala Gln
            260                 265                 270

Ala Gln Ala Leu Arg Ala Ser Leu Ala Val Ile Arg Ser Asp Glu Gly
        275                 280                 285

Asp Ala Arg Arg Glu Lys Leu Ala Ala Leu Ile Thr Arg Phe Arg Ala
    290                 295                 300

Gly Val Gln Asp Leu Pro Phe Thr Leu Ala Asp Ser Cys Ser Ala Ile
```

```
                305                 310                 315                 320
Gln Pro Leu Ile Val Gly Asp Asn Ser Arg Ala Leu Gln Leu Ala Glu
                    325                 330                 335

Lys Leu Arg Gln Gln Gly Cys Trp Val Thr Ala Ile Arg Pro Pro Thr
                340                 345                 350

Val Pro Ala Gly Thr Ala Arg Leu Arg Leu Thr Leu Thr Ala Ala His
                355                 360                 365

Glu Met Gln Asp Ile Asp Arg Leu Leu Glu Val Leu His Gly Asn Gly
            370                 375                 380

<210> SEQ ID NO 3
<211> LENGTH: 429
<212> TYPE: PRT
<213> ORGANISM: Escherichia coli
<220> FEATURE:
<223> OTHER INFORMATION: E. coli strain K-12, substrain W3110
      PLP-dependent 7,8-diaminopelargonic acid (DAPA) synthase, bioA
      gene product

<400> SEQUENCE: 3

Met Thr Thr Asp Asp Leu Ala Phe Asp Gln Arg His Ile Trp His Pro
1               5                   10                  15

Tyr Thr Ser Met Thr Ser Pro Leu Pro Val Tyr Pro Val Val Ser Ala
                20                  25                  30

Glu Gly Cys Glu Leu Ile Leu Ser Asp Gly Arg Arg Leu Val Asp Gly
            35                  40                  45

Met Ser Ser Trp Trp Ala Ala Ile His Gly Tyr Asn His Pro Gln Leu
        50                  55                  60

Asn Ala Ala Met Lys Ser Gln Ile Asp Ala Met Ser His Val Met Phe
65                  70                  75                  80

Gly Gly Ile Thr His Ala Pro Ala Ile Glu Leu Cys Arg Lys Leu Val
                85                  90                  95

Ala Met Thr Pro Gln Pro Leu Glu Cys Val Phe Leu Ala Asp Ser Gly
            100                 105                 110

Ser Val Ala Val Glu Val Ala Met Lys Met Ala Leu Gln Tyr Trp Gln
        115                 120                 125

Ala Lys Gly Glu Ala Arg Gln Arg Phe Leu Thr Phe Arg Asn Gly Tyr
            130                 135                 140

His Gly Asp Thr Phe Gly Ala Met Ser Val Cys Asp Pro Asp Asn Ser
145                 150                 155                 160

Met His Ser Leu Trp Lys Gly Tyr Leu Pro Glu Asn Leu Phe Ala Pro
                165                 170                 175

Ala Pro Gln Ser Arg Met Asp Gly Glu Trp Asp Glu Arg Asp Met Val
            180                 185                 190

Gly Phe Ala Arg Leu Met Ala Ala His Arg His Glu Ile Ala Ala Val
        195                 200                 205

Ile Ile Glu Pro Ile Val Gln Gly Ala Gly Gly Met Arg Met Tyr His
    210                 215                 220

Pro Glu Trp Leu Lys Arg Ile Arg Lys Ile Cys Asp Arg Glu Gly Ile
225                 230                 235                 240

Leu Leu Ile Ala Asp Glu Ile Ala Thr Gly Phe Gly Arg Thr Gly Lys
                245                 250                 255

Leu Phe Ala Cys Glu His Ala Glu Ile Ala Pro Asp Ile Leu Cys Leu
            260                 265                 270

Gly Lys Ala Leu Thr Gly Gly Thr Met Thr Leu Ser Ala Thr Leu Thr
        275                 280                 285
```

```
Thr Arg Glu Val Ala Glu Thr Ile Ser Asn Gly Glu Ala Gly Cys Phe
        290                 295                 300

Met His Gly Pro Thr Phe Met Gly Asn Pro Leu Ala Cys Ala Ala Ala
305                 310                 315                 320

Asn Ala Ser Leu Ala Ile Leu Glu Ser Gly Asp Trp Gln Gln Gln Val
                325                 330                 335

Ala Asp Ile Glu Val Gln Leu Arg Glu Gln Leu Ala Pro Ala Arg Asp
            340                 345                 350

Ala Glu Met Val Ala Asp Val Arg Val Leu Gly Ala Ile Gly Val Val
        355                 360                 365

Glu Thr Thr His Pro Val Asn Met Ala Ala Leu Gln Lys Phe Phe Val
    370                 375                 380

Glu Gln Gly Val Trp Ile Arg Pro Phe Gly Lys Leu Ile Tyr Leu Met
385                 390                 395                 400

Pro Pro Tyr Ile Ile Leu Pro Gln Gln Leu Gln Arg Leu Thr Ala Ala
                405                 410                 415

Val Asn Arg Ala Val Gln Asp Glu Thr Phe Phe Cys Gln
            420                 425

<210> SEQ ID NO 4
<211> LENGTH: 225
<212> TYPE: PRT
<213> ORGANISM: Escherichia coli
<220> FEATURE:
<223> OTHER INFORMATION: E. coli strain K-12, substrain W3110
      dethiobiotin synthase (DTB synthase 1, DTBS 1), bioD gene product
      (BIOD, BioD)

<400> SEQUENCE: 4

Met Ser Lys Arg Tyr Phe Val Thr Gly Thr Asp Thr Glu Val Gly Lys
1               5                   10                  15

Thr Val Ala Ser Cys Ala Leu Leu Gln Ala Ala Lys Ala Ala Gly Tyr
            20                  25                  30

Arg Thr Ala Gly Tyr Lys Pro Val Ala Ser Gly Ser Glu Lys Thr Pro
        35                  40                  45

Glu Gly Leu Arg Asn Ser Asp Ala Leu Ala Leu Gln Arg Asn Ser Ser
    50                  55                  60

Leu Gln Leu Asp Tyr Ala Thr Val Asn Pro Tyr Thr Phe Ala Glu Pro
65                  70                  75                  80

Thr Ser Pro His Ile Ile Ser Ala Gln Glu Gly Arg Pro Ile Glu Ser
                85                  90                  95

Leu Val Met Ser Ala Gly Leu Arg Ala Leu Glu His Lys Ala Asp Trp
            100                 105                 110

Val Leu Val Glu Gly Ala Gly Gly Trp Phe Thr Pro Leu Ser Asp Thr
        115                 120                 125

Phe Thr Phe Ala Asp Trp Val Thr Gln Glu Gln Leu Pro Val Ile Leu
    130                 135                 140

Val Val Gly Val Lys Leu Gly Cys Ile Asn His Ala Met Leu Thr Ala
145                 150                 155                 160

Gln Val Ile Gln His Ala Gly Leu Thr Leu Ala Gly Trp Val Ala Asn
                165                 170                 175

Asp Val Thr Pro Pro Gly Lys Arg His Ala Glu Tyr Met Thr Thr Leu
            180                 185                 190

Thr Arg Met Ile Pro Ala Pro Leu Leu Gly Glu Ile Pro Trp Leu Ala
        195                 200                 205
```

-continued

Glu Asn Pro Glu Asn Ala Ala Thr Gly Lys Tyr Ile Asn Leu Ala Leu
    210                 215                 220

Leu
225

<210> SEQ ID NO 5
<211> LENGTH: 346
<212> TYPE: PRT
<213> ORGANISM: Escherichia coli
<220> FEATURE:
<223> OTHER INFORMATION: E. coli strain K-12, substrain W3110 biotin
      synthase, bioB gene product

<400> SEQUENCE: 5

Met Ala His Arg Pro Arg Trp Thr Leu Ser Gln Val Thr Glu Leu Phe
1               5                   10                  15

Glu Lys Pro Leu Leu Asp Leu Leu Phe Glu Ala Gln Gln Val His Arg
            20                  25                  30

Gln His Phe Asp Pro Arg Gln Val Gln Val Ser Thr Leu Leu Ser Ile
        35                  40                  45

Lys Thr Gly Ala Cys Pro Glu Asp Cys Lys Tyr Cys Pro Gln Ser Ser
    50                  55                  60

Arg Tyr Lys Thr Gly Leu Glu Ala Glu Arg Leu Met Glu Val Glu Gln
65                  70                  75                  80

Val Leu Glu Ser Ala Arg Lys Ala Lys Ala Ala Gly Ser Thr Arg Phe
                85                  90                  95

Cys Met Gly Ala Ala Trp Lys Asn Pro His Glu Arg Asp Met Pro Tyr
            100                 105                 110

Leu Glu Gln Met Val Gln Gly Val Lys Ala Met Gly Leu Glu Ala Cys
        115                 120                 125

Met Thr Leu Gly Thr Leu Ser Glu Ser Gln Ala Gln Arg Leu Ala Asn
    130                 135                 140

Ala Gly Leu Asp Tyr Tyr Asn His Asn Leu Asp Thr Ser Pro Glu Phe
145                 150                 155                 160

Tyr Gly Asn Ile Ile Thr Thr Arg Thr Tyr Gln Glu Arg Leu Asp Thr
                165                 170                 175

Leu Glu Lys Val Arg Asp Ala Gly Ile Lys Val Cys Ser Gly Gly Ile
            180                 185                 190

Val Gly Leu Gly Glu Thr Val Lys Asp Arg Ala Gly Leu Leu Leu Gln
        195                 200                 205

Leu Ala Asn Leu Pro Thr Pro Pro Glu Ser Val Pro Ile Asn Met Leu
    210                 215                 220

Val Lys Val Lys Gly Thr Pro Leu Ala Asp Asn Asp Val Asp Ala
225                 230                 235                 240

Phe Asp Phe Ile Arg Thr Ile Ala Val Ala Arg Ile Met Met Pro Thr
                245                 250                 255

Ser Tyr Val Arg Leu Ser Ala Gly Arg Glu Gln Met Asn Glu Gln Thr
            260                 265                 270

Gln Ala Met Cys Phe Met Ala Gly Ala Asn Ser Ile Phe Tyr Gly Cys
        275                 280                 285

Lys Leu Leu Thr Thr Pro Asn Pro Glu Glu Asp Lys Asp Leu Gln Leu
    290                 295                 300

Phe Arg Lys Leu Gly Leu Asn Pro Gln Gln Thr Ala Val Leu Ala Gly
305                 310                 315                 320

```
Asp Asn Glu Gln Gln Gln Arg Leu Glu Gln Ala Leu Met Thr Pro Asp
                325                 330                 335
Thr Asp Glu Tyr Tyr Asn Ala Ala Ala Leu
            340                 345
```

HYBRID POLYKETIDE SYNTHASES

This application is the U.S. National Stage entry of International Application No. PCT/US2011/058660, filed Oct. 31, 2011, which claims benefit of priority to U.S. provisional application No. 61/408,411, filed Oct. 29, 2010, each of which application is herein incorporated by reference for all purposes.

STATEMENT AS TO RIGHTS TO INVENTIONS MADE UNDER FEDERALLY SPONSORED RESEARCH OR DEVELOPMENT

This invention was made with government support under Contract No. DE-AC02-05CH11231 awarded by the U.S. Department of Energy and Award No. 0540879 awarded by the National Science Foundation. The government has certain rights in the invention

REFERENCE TO A "SEQUENCE LISTING SUBMITTED AS A TEXT FILE

The Sequence Listing written in file SEQTXT_77429-865771-010110US.txt, created on Apr. 22, 2013, 14,668 bytes, machine format IBM-PC, MS-Windows operating system, is hereby incorporated by reference.

FIELD OF THE INVENTION

This invention relates to the production of useful compounds with polyketide synthases.

BACKGROUND OF THE INVENTION

Dicarboxylic acids (diacids) are important compounds that are used in the manufacture of commercial polymers (e.g. polyesters, polyurethanes). The use of hybrid polyketide synthases to produce diacids having a carbon backbone with an odd number of carbon atoms is disclosed in International Patent Application Publication No. WO 2009/121066. However, commercial polymers are typically produced from reactants derived from petroleum and petrochemicals.

For example, as illustrated in FIG. 1, the dicarboxylic acid adipic acid [1] is used mainly as a monomer in the production of nylon 6,6 [2], a polyamide generated through the reaction of [1] with hexane-1,6-diamine. Polyesters (for use in fabrics and plastics of many compositions) are formed through the polymerization of terephthalic acid [3] and a dialcohol (diol) such as ethylene glycol (to make polyethylene terephthalate [4]), propane diol (poly(1,3-propanediol terephthalate) [5]) or butanediol (poly(1,4-butanediolphthalate) [6]. Adipic acid is also used in the synthesis of various polyesters. Currently adipic acid is synthesized via oxidation of cyclohexane and similar petrochemicals using traditional chemical synthesis.

Lactams are important compounds useful in the manufacture of a variety of compounds, including commercial polymers, particularly polyamides such as Nylon 6 and Nylon 12. Caprolactam is the sole source of Nylon 6, which is used in the production of durable fibers for carpets and in other products. Larger chain lactams, such as Nylon 12, are used in engineering plastics where their physical properties make them more desirable. The open chain form of these molecules are also accessible using the technology described herein. These cognate acids are also used in many of the same applications. For example, 6-aminohexanoic acid is the open chain form of caprolactam and can also be polymerized to produce Nylon 6.

Diamines are used extensively in the production of polymers, predominantly Nylons, as described above.

The large scale worldwide use of nylons and polyesters requires the production of millions of metric tons of adipic acid, caprolactam and 1,6-hexanediamine annually. The diacids, lactams, and diamines are themselves synthesized from starting materials extracted from petroleum. There is a need for new methods to synthesize such compounds in a manner that reduces dependence on oil.

Complex polyketides comprise a large class of natural products that are synthesized in bacteria (mainly members actinomycete family; e.g. *Streptomyces*), fungi and plants. Polyketides form the aglycone component of a large number of clinically important drugs, such as antibiotics (e.g. erythromycin, tylosin), antifungal agents (e.g. nystatin), anticancer agents (e.g. epothilone), immunosuppressives (e.g. rapamycin), etc. Though these compounds do not resemble each other either in their structure or their mode of action, they share a common basis for their biosynthesis, which is carried out by a group of enzymes designated polyketide synthases. Polyketide synthases (PKS) employ short chain fatty acyl CoAs in Claisen condensation reactions to produce polyketides. Unlike fatty acid synthases, which utilize acetyl CoA as the starter and malonyl CoA as the extender units and which use a single module iteratively to produce the nascent acyl chains, PKSs are composed of multiple, discrete modules, each catalyzing the chain growth of a single step. The present invention provides methods and compositions for employing polyketide synthases to produce diacids, lactams, diamines, e.g., for the production of commercial polymers.

BRIEF SUMMARY OF THE INVENTION

The present invention provides for a polyketide synthase (PKS), and/or optionally non-ribosomal peptide synthase and/or CoA ligase, capable of synthesizing an even-chain or odd-chain diacid or lactam or diamine. The PKS is not a naturally occurring PKS. In some embodiments of the invention, the even-chain or odd-chain diacid or lactam or diamine is not a compound synthesized by a naturally occurring PKS. In some embodiments of the invention, the PKS is a hybrid PKS comprising modules, domains, and/or portions thereof from two or more naturally occurring PKSs.

The present invention also provides for a recombinant nucleic acid that encodes a polyketide synthase (PKS) of the present invention. The recombinant nucleic acid can be replicon capable of stable maintenance in a host cell. In some embodiments, the replicon is stably integrated into a chromosome of the host cell. In some embodiments, the replicon is a plasmid. The present invention also provides for a vector or expression vector comprising a recombinant nucleic acid of the present invention. The present invention additionally provides for a host cell comprising any of the recombinant nucleic acid and/or PKS of the present invention. In some embodiments, the host cell, when cultured under a suitable condition, is capable of producing an even- or odd-chain diacid, lactam, or diamine.

The present invention provides a method of producing an even-chain or odd-chain diacid or lactam or diamine, comprising: providing a host cell of the present invention, and culturing said host cell in a suitable culture medium such that the even-chain or odd-chain diacid or lactam or diamine is produced.

The present invention provides for a composition comprising an even-chain or odd-chain diacid or lactam or diamine isolated from a host cell from which the even-chain or odd-chain diacid or lactam or diamine was produced, and trace residues and/or contaminants of the host cell. Such trace residues and/or contaminants include cellular material produced by the lysis of the host cell. In some embodiments of the invention, the trace residues and/or contaminants do not or essentially do not interfere or retard a polymerization reaction involving the even-chain or odd-chain diacid or lactam or diamine. The present invention also provides these compounds in substantially pure form as well as methods for using these compounds to make other useful compounds, such as commercial polymers.

The present invention provides for a polyketide synthase (PKS) capable of synthesizing malonic acid. The present invention provides for a recombinant nucleic acid that encodes a polyketide synthase (PKS) capable of synthesizing malonic acid. The present invention provides for a host cell comprising any of the recombinant nucleic acid and/or PKS of the present invention, wherein when cultured under a suitable condition the host cell is capable of producing malonic acid. The present invention provides a method of producing malonic acid, comprising: providing a host cell of the present invention, and culturing said host cell in a suitable culture medium such that the malonic acid is produced. The present invention provides for a composition comprising a malonic acid isolated from a host cell from which the malonic acid is produced, and trace residues and/or contaminants of the host cell.

The present invention provides for a polyketide synthase (PKS) capable of synthesizing pimelic acid, 7-keto-8-amino-pelargonic acid (KAPA), or biotin. The present invention provides for a recombinant nucleic acid that encodes a polyketide synthase (PKS) capable of synthesizing pimelic acid (KAPA). The present invention provides for a host cell comprising any of the recombinant nucleic acid and/or PKS of the present invention, wherein when cultured under a suitable condition the host cell is capable of producing the pimelic acid or KAPA, and optionally biotin. The present invention provides a method of producing pimelic acid or KAPA, and optionally biotin, comprising: providing a host cell of the present invention, and culturing said host cell in a suitable culture medium such that the pimelic acid or KAPA, and optionally biotin, is produced. The present invention provides for a composition comprising a pimelic acid or KAPA, and optionally biotin, isolated from a host cell from which the pimelic acid or KAPA, and optionally biotin, is produced, and trace residues and/or contaminants of the host cell.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1:
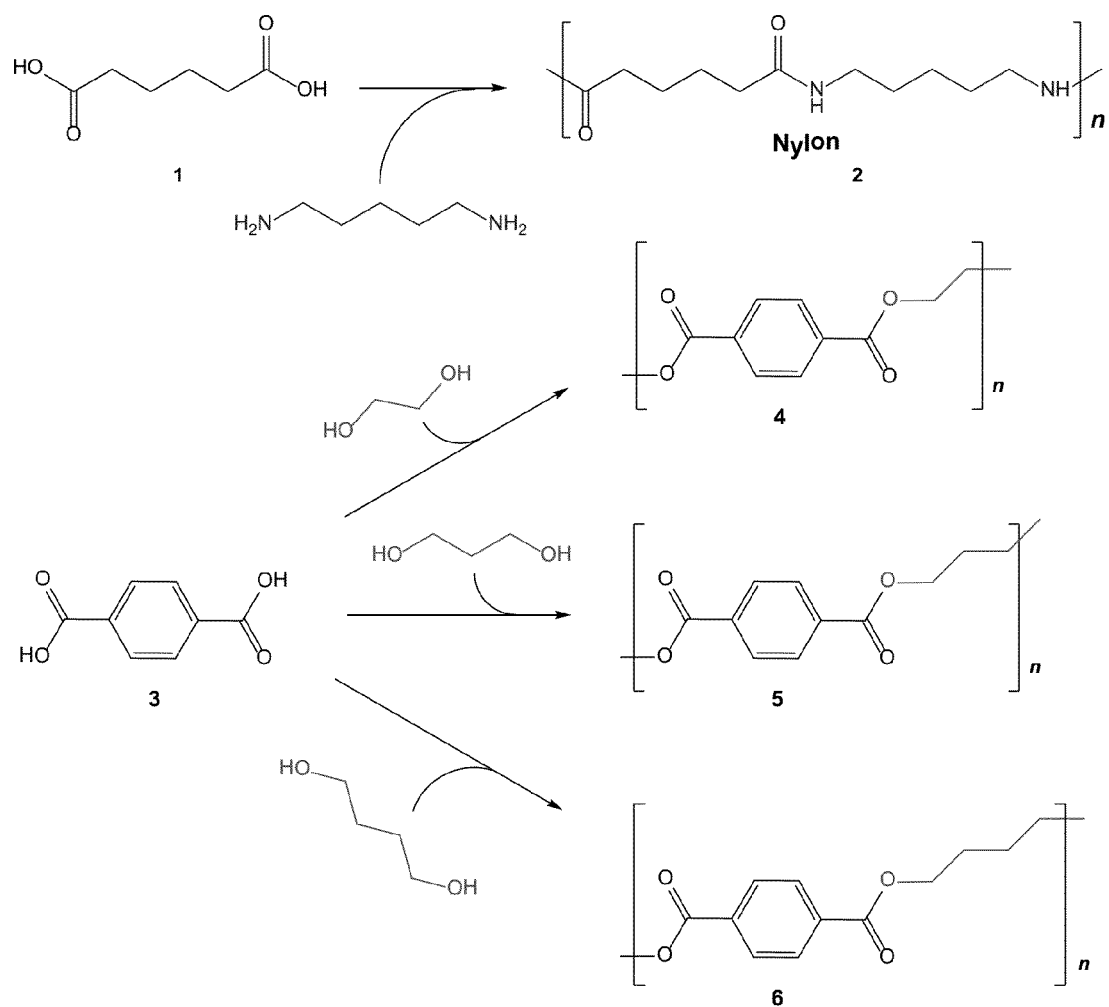
FIG. 1 shows the various reactions using diacids in the manufacture of commercial polymers (e.g. polyesters, polyurethanes). The diacid adipic acid [1] is used as a monomer in the production of nylon [2], a polyamide generated through the reaction of [1] with hexane-1,6-diamine. Polyesters are formed through the polymerization of terephthalic acid [3] and a dialcohol (diol) such as ethylene glycol (to make polyethylene terephalate [4]), propane diol (poly(1,3-propanediol terephthalate) [5]) or butanediol (poly(1,4-butanediolphthalate) [6].

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any method's and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a diacid" includes a plurality of such diacids, and so forth.

The term "diacid" refers to a hydrocarbon possessing two carboxylic acid moieties bridged by a chain, or backbone, or one or more carbons. The branching and oxidative state of the carbon backbone is variable, as described within.

The term "even-chain diacid" refers to a diacid with a carbon backbone, i.e., disregarding any functional groups or substituents, with an even number of carbon atoms.

The term "odd-chain diacid" refers to a diacid with a carbon backbone, i.e., disregarding any functional groups or substituents, with an odd number of carbon atoms.

The term "lactam" refers to a heterolcyclic hydrocarbon containing an amide bond in the ring. The technology described herein allows the production of either the lactam or the cognate acid form to any lactam described (e.g. 6-aminohexanoic acid is the cognate acid of caprolactam). The terms "open chain lactam" or "lactam cognate acid" are used to describe the hydrolyzed form of the lactam, a hydrocarbon chain possessing a carboxylate at one end and a pendent amino group. The term "lactam" as used herein encompasses both of these chemical classes. Like the diacids, the branching and oxidative state of the carbons in the backbone is controlled as described herein. The lactams contain even or odd numbers of carbon atoms in the carbon backbone.

The term "diamine" refers to two amine moieties bridged by a hydrocarbon chain, or backbone, or one or more carbons. As is the case with the diacids and lactams, the branching and oxidative state of the carbon backbone is variable by design, as described herein. "Diamine" refers to a diamine with a carbon backbone, i.e., disregarding any functional groups or substituents, with an odd or even number of carbon atoms.

The term "functional variant" describes an enzyme that has a polypeptide sequence that is at least 70%, 75%, 80%, 85%, 90%, 95% or 99% identical to any one of the enzymes described herein. The "functional variant" enzyme may retain amino acids residues that are recognized as conserved for the enzyme, and may have non-conserved amino acid residues substituted or found to be of a different amino acid, or amino acid(s) inserted or deleted, but which does not affect or has insignificant effect its enzymatic activity as compared to the enzyme described herein. The "functional variant" enzyme has an enzymatic activity that is identical or essentially identical to the enzymatic activity of the enzyme described herein. The "functional variant" enzyme may be found in nature or be an engineered mutant thereof.

These and other objects, advantages, and features of the invention will become apparent to those persons skilled in the art upon reading the details of the invention as more fully described below.

Polyketide Synthases (PKS)

The present invention provides for a polyketide synthase (PKS) or PKS/non-ribosomal peptide synthetase (NRPS) hybrid capable of synthesizing an even-chain or odd-chain diacid, or lactam, or diamine. The PKS or PK/NRPS is not naturally occurring. In some embodiments of the invention, the even-chain or odd-chain diacid, or lactam, or diamine is not a compound synthesized by a naturally occurring PKS or PKS/NRPS. In some embodiments of the invention, the PKS is a hybrid PKS comprising modules, domains, and/or portions thereof from two or more PKSs. Such even-chain or odd-chain diacids, or lactams, or diamines include the diketides and triketides, and polyketides of more than three ketide units, such as 4, 5, or 6 or more ketide units. The even-chain or odd-chain diacids, or lactams, or diamines can further include one or more functional groups. Such functional groups include, but are not limited to, ethyl, methyl and hydroxyl side chains, and internal olefins and ketones.

Figure 2:
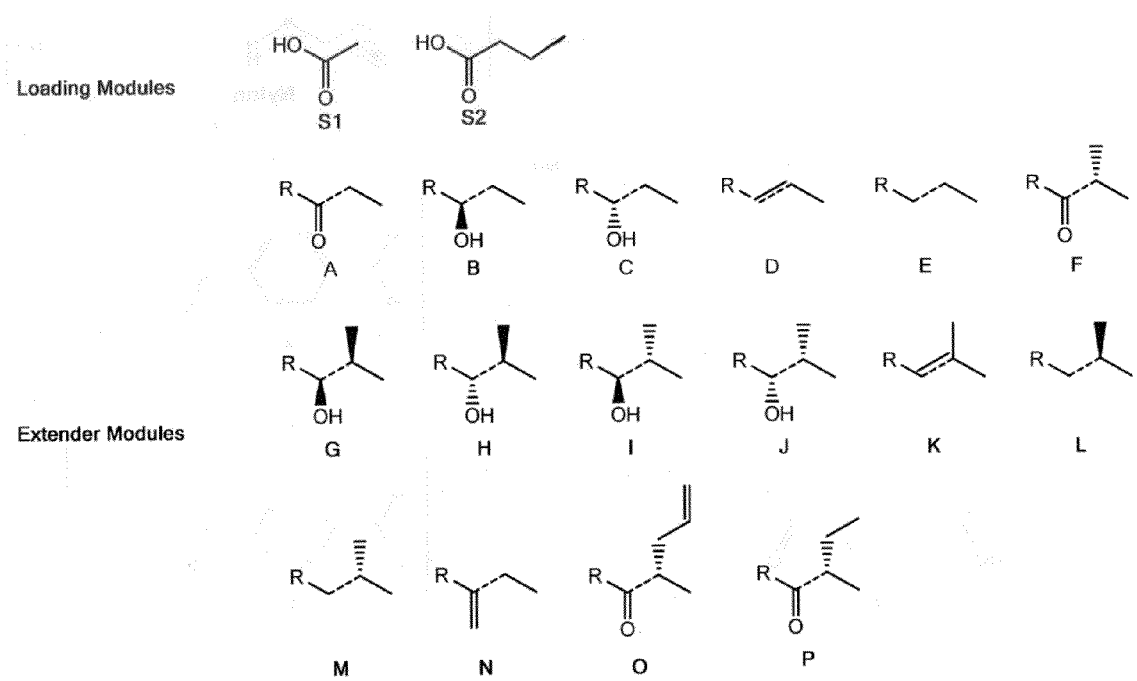
FIG. 2 shows types of modules employed and corresponding precursors utilized for incorporation into polyketide chains. The loading module is designated S. The remaining compounds represent the structures incorporated into the growing polyketide chain employing extender modules A-P. The dashed line indicates the C—C bond formed through Claisen condensation; atoms to the right of the bond and the C atom at the left of the dashed line represent the structures determined by the module employed. The R group represents the existing acyl chain prior to incorporation determined by the module.
Figure 3:
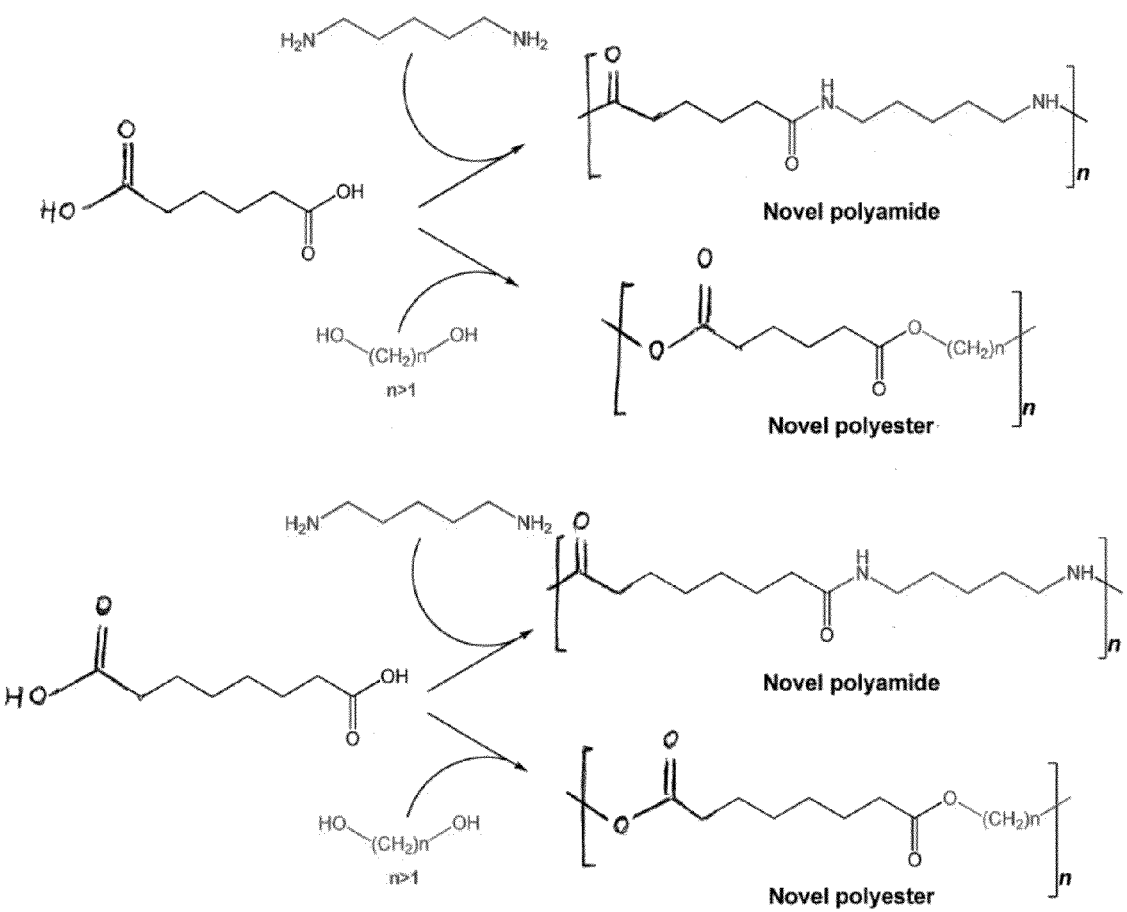
FIG. 3 shows a scheme for making polyamides or polyesters using even-chain diacids.

PKSs employ short chain fatty acyl CoAs in Claisen condensation reactions to produce polyketides. Unlike fatty acid synthases which utilize acetyl CoA as the starter and malonyl CoA as the extender units, and use a single module iteratively to produce the nascent acyl chains, PKSs are composed of discrete modules, each catalyzing the chain growth of a single step. Modules can differ from each other in composition so that overall, a number of different starters (e.g. acetyl CoA, propionyl CoA) and extenders, some of which contain stereospecific methyl (or ethyl) side chains can be incorporated. In addition, PKS modules do not always reduce the 3-carbonyl formed from condensation but may leave it either unreduced (ketone), partially reduced (hydroxyl, 2,3-ene) or fully reduced (3-methylene). Many polyketide synthases employ malonyl CoA or [S]-2-methylmalonyl CoA as the starter for polyketide synthesis. In such cases the terminal carboxyl group is usually removed by a decarboxylase domain present at the N-terminus of the corresponding loading domain of the PKS. In summary, the structure (and chirality) of the α-carbon and β-carbonyl is determined by the module of the PKS employed in the synthesis of the growing chain at each particular step. Because of the correspondence between use of modules in the synthesis and the structure of the polyketide produced, it is possible to program the synthesis to produce a compound of desired structure by selection and genetic manipulation of polyketide synthases. FIG. 2 shows the various modules and the precursor utilized by each module for incorporation into the corresponding nascent acyl (polyketide) chain to give rise to the range of compounds of interest. Table 1 provides a PKS source for each module. Each PKS source is well-known to one skilled in the art is readily available. In addition, for each module taught in Table 1, there may be many other modules from other PKS that can be used.

TABLE 1

PKS sources of the various modules.

| Module | PKS Source |
| --- | --- |
| S1 | Spirofungin PKS Loading Domain |
| S2 | Chondrochloren PKS Loading Domain (with CoA ligase domain replaced with Succinyl CoA Ligase) |
| A | Rifamycin PKS Module 2 |
| B | Oligomycin PKS Module 1 |
| C | Spiramycin PKS Module 1 |
| D | Pikromycin PKS Module 2 |
| E | Oligomycin PKS Module 3 |
| F | Erythromycin PKS Module 3 |
| G | Oligomycin PKS Module 5 |
| H | Primaricin PKS Module 7 |
| I | Tylosin PKS Module 1 |
| J | Erythromycin PKS Module 1 |
| K | Avermectin PKS Module 7 |
| L | Rapamycin PKS Module 1 |
| M | Erythromycin PKS Module 4 |
| N | Pederin Module 2 |
| O | Ascomycin Module 4 |
| P | FK506 Module 4 |

All extender modules carry the β-acyl ACP synthase (commonly called the ketosynthase or KS) domain, which conducts the decarboxylative condensation step between the extender and the growing polyketide chain, and the acyl carrier protein (ACP) domain that carries the growing acyl chain and presents it to the cognate reductive domains for reduction of the β-carbonyl. Modules can differ from each other in composition so that a number of different starter and extender units, some of which contain stereospecific side chains (e.g. methyl, ethyl, propylene) can be incorporated. The acyltransferase (AT) domain of each module determines the extender unit (e.g. malonyl CoA, methylmalonyl CoA, etc.) incorporated. In addition, PKS modules do not always reduce the β-carbonyl formed from condensation but may leave it either unreduced (ketone), partially reduced (hydroxyl, 2,3-ene) or fully reduced (3-methylene), as shown in FIG. 2. The ketoreductase (KR) domain reduces the ketone to the OH function (stereospecifically); the dehydratase (DH) domain removes water from the α and β carbons leaving an α,β trans-double bond; the enoylreductase (ER) domain reduces the double bond to a β-methylene center; the reductive state of the β-carbonyl, therefore, is determined by the presence of functional reductive domains in the corresponding module. Less commonly, modules are found to contain an additional C-methylation domain (yielding an additional α-methyl side chain, as in epothilone). The makeup of the PKS, therefore, determines the choice of starter and extender acyl units incorporated, the extent of reduction at each condensation step, and the total number of units added to the chain. The wide diversity of structures of polyketides seen in nature is attributed to the diversity in PKS compositions.

A partial list of sources of PKS sequences that can be used in making the PKSs of the present invention, for illustration and not limitation, includes Ambruticin (U.S. Pat. No. 7,332,576); Avermectin (U.S. Pat. No. 5,252,474; MacNeil et al., 1993, *Industrial Microorganisms: Basic and Applied Molecular Genetics*, Baltz, Hegeman, & Skatrud, eds. (ASM), pp. 245-256; MacNeil et al., 1992, *Gene* 115: 119-25); Candicidin (FRO008) (Hu et al., 1994, *Mol. Microbiol.* 14: 163-72); Epothilone (U.S. Pat. No. 6,303,342); Erythromycin (WO 93/13663; U.S. Pat. No. 5,824,513; Donadio et al., 1991, *Science* 252:675-79; Cortes et al., 1990, *Nature* 348:176-8); FK506 (Motamedi et al., 1998, *Eur. J. Biochem.* 256:528-34; Motamedi et al., 1997, *Eur. J. Biochem.* 244:74-80); FK520 or ascomycin (U.S. Pat. No. 6,503,737; see also Nielsen et al., 1991, *Biochem.* 30:5789-96); Jerangolid (U.S. Pat. No. 7,285,405); Leptomycin (U.S. Pat. No. 7,288,396); Lovastatin (U.S. Pat. No. 5,744,350); Nemadectin (MacNeil et al., 1993, supra); Niddamycin (Kakavas et al., 1997, *J. Bacteriol.* 179:7515-22); Oleandomycin (Swan et al., 1994, *Mol. Gen. Genet.* 242:358-62; U.S. Pat. No. 6,388,099; Olano et al., 1998, *Mol. Gen. Genet.* 259:299-308); Pederin (PCT publication no. WO 2003/044186); Pikromycin (Xue et al., 2000, *Gene* 245:203-211); Pimaricin (PCT publication no. WO 2000/077222); Platenolide (EP Pat. App. 791,656); Rapamycin (Schwecke et al., 1995, *Proc. Natl. Acad. Sci. USA* 92:7839-43); Aparicio et al., 1996, *Gene* 169:9-16); Rifamycin (August et al., 1998, *Chemistry & Biology*, 5: 69-79); Soraphen (U.S. Pat. No. 5,716,849; Schupp et al., 1995, *J. Bacteriology* 177: 3673-79); Spiramycin (U.S. Pat. No. 5,098,837); Tylosin (EP 0 791,655; Kuhstoss et al., 1996, *Gene* 183:231-36; U.S. Pat. No. 5,876,991). Additional suitable PKS coding sequences are readily available to one skilled in the art, or remain to be discovered and characterized, but will be available to those of skill (e.g., by reference to GenBank). Each of the references cited is hereby specifically and individually incorporated by reference.

Of the more than one hundred PKSs examined, the correspondence between use of modules in the biosynthesis and the structure of the polyketide produced is fully understood both at the level of the protein sequence of the PKS and the DNA sequence of the corresponding genes. The programming of modules into polyketide structure can be identified by sequence determination. It is possible to clone or synthesize DNA sequences corresponding to desired modules and transfer them as fully functioning units to heterologous, otherwise non-polyketide producing hosts such as *E. coli* (B. A. Pfeifer, S. J. Admiraal, H. Gramajo, D. E. Cane, C. Khosla, *Science* 291, 1790 (2001); hereby incorporated by reference) and *Streptomyces* (C. M. Kao, L. Katz, C. Khosla, *Science* 265, 509 (1994); hereby incorporated by reference). Additional genes employed for polyketide biosynthesis have also been identified. Genes that determine phosphopantetheine:protein transferase (PPTase) that transfer the 4-phosphopantetheine co-factor of the ACP domains, commonly present in polyketide producing hosts, have been cloned in *E. coli* and other hosts (K. J. Weissman, H. Hong, M. Oliynyk, A. P. Siskos, P. F. Leadlay, *Chembiochem* 5, 116 (2004); hereby incorporated by reference). It is also possible to re-program polyketide biosynthesis to produce a compound of desired structure by either genetic manipulation of a single PKS or by construction of a hybrid PKS composed of modules from two or more sources (K. J. Weissman, H. Hong, M. Oliynyk, A. P. Siskos, P. F. Leadlay, *Chembiochem* 5, 116 (2004); hereby incorporated by reference).

Recombinant methods for manipulating modular PKS genes to make the PKSs of the present invention are described in U.S. Pat. Nos. 5,672,491; 5,843,718; 5,830,750; 5,712,146; and 6,303,342; and in PCT publication nos. WO 98/49315 and WO 97/02358; hereby incorporated by reference. A number of genetic engineering strategies have been used with various PKSs to demonstrate that the structures of polyketides can be manipulated to produce novel polyketides (see the patent publications referenced supra and Hutchinson, 1998, *Curr. Opin. Microbiol.* 1:319-329, and Baltz, 1998, *Trends Microbiol.* 6:76-83; hereby incorporated by reference). In some embodiments, the components of the hybrid PKS are arranged onto polypeptides having interpolypeptide linkers that direct the assembly of the polypeptides into the functional PKS protein, such that it is not required that the PKS have the same arrangement of modules in the polypeptides as observed in natural PKSs. Suitable interpolypeptide linkers to join polypeptides and intrapolypeptide linkers to join modules within a polypeptide are described in PCT publication no. WO 00/47724, hereby incorporated by reference.

Figure 27:
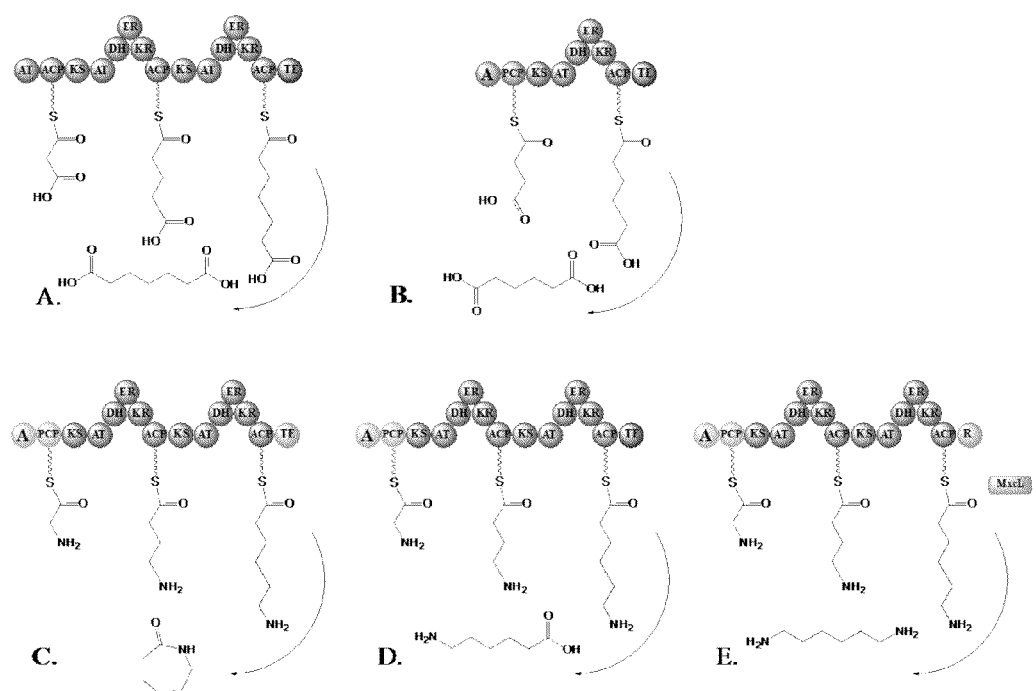
FIG. 27A-27E provides a general schematic for producing odd and even chain diacids, lactams and cognate acids, and diamines.

FIG. 27 provides a schematic for the hybrid PKS of the invention used for producing the odd chain diacids (A) and even chain diacids (B), lactams (C) and cognate amino acids (D), and diamines (E). By changing the chemistry incorporated at the start of the process, the terminal functionality (acid or amine) and odd vs. even number of carbons in the linear backbone is established. The number and composition of the intervening modules dictates the total number of carbons as well as the branching and oxidative state of the carbon chain. The chain release mechanism of the TE domain, or R+MxcL in the case of *E. coli*, is responsible for the final form of the molecule as a free acid, lactam, amino acid or diamine. In FIG. 27A, the system loads malonate and extends with two additional malonate (each from malonyl-CoA) using a full reductive cycle with each extension. In this example, a hydrolytic TE domain is used to release the free carboxylate, in this case pimelic acid. In FIG. 27B, the system incorporates succinate using an NRPS loading module, then extends with malonate and fully reduces intermediate, then releases adipic acid. Thus, by changing the loading module and module depicted in FIG. 27A to the NRPS illustrated in FIG. 27B, the chain length and odd vs. even carbon count is also changed. By switching the malonate loading module depicted in FIG. 27A to an NRPS loading module specific for glycine, 6-aminohexanoic acid can be made, as illustrated in FIG. 27D. By changing the thioesterase domain depicted in FIG. 27D to one known to catalyze lactonization, the same system can release the product as a lactam, as shown in FIG. 27C. If this thioesterase is changed to an R domain and complemented with an amino transferase, such as MxcL, the same system can be used to biosynthesize hexane-1,6-diamine (FIG. 27E).

In some embodiments of the invention, the even-chain diacid has the following chemical structure:

(I)

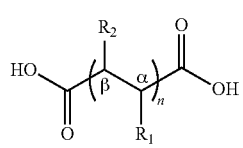

wherein each $R_1$ is independently H, OH, $OCH_3$, $CH_2CH_3$, or $CH_3$, each $R_2$ is independently a carbonyl, H or OH, n is an integer, αβ is (1) a single bond or (2) a double bond, with the proviso that when an αβ is a double bond then the corresponding $R_2$ is H and n indicates the number of two-carbon-chain subunits in the carbon backbone of the even-chain diacid. Within each molecule of the even-chain diacid, the $R_1$, $R_2$, and αβ within each two-carbon-subunit can be independent of (and so can be identical to or different from) the $R_1$, $R_2$, and αβ of every other two-carbon-subunit of the molecule. For example, chemical structure (1) encompasses (2E, 8E)-deca-2,8-dienedioic acid (using oxylate as a loading molecule):

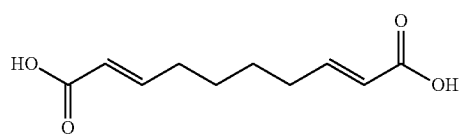 [SMILES: O=C(O)/C=C/CCCC/C=C/C(=O)O]

In some embodiments of the invention, n is an integer from 1 to 10. In some embodiments of the invention, the even-chain diacid is adipic acid (or hexanedioc acid), suberic acid (or octanedioc acid), or sebacic acid (or decanedioc acid). In some embodiments of the invention, the even-chain diacid is a symmetrical compound, such as a fully reduced symmetrical aliphatic compound.

Adipic acid is a six carbon chain fully reduced symmetrical aliphatic compound with no side chains, hence no chiral centers. Diacids of a (4+n)-configuration are synthesized from the NRPS-PKS system of the present invention, a four carbon succinate is extended by n extender acyl unit(s). For example, when a six-membered chain is synthesized from the NRPS-PKS system of the present invention, a four carbon succinate is extended by one extender acyl unit. For example, when a ten-membered chain is synthesized from the NRPS-PKS system of the present invention, a four carbon succinate is extended by two extender acyl units.

In some embodiments of the invention, the odd-chain diacid has the following chemical structure:

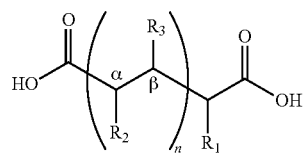

wherein each $R_1$ and $R_2$ are independently H, OH, $OCH_3$, $CH_2CH_3$, or $CH_3$, each $R_3$ is independently a carbonyl, H or OH, n is an integer from 0 to 10 and represents the addition of two carbons to the polyketide chain, αβ is (1) a single bond or (2) a double bond, with the proviso that when an αβ is a double bond then the corresponding $R_3$ is H, and n indicates the number of two-carbon-chain subunits in the carbon backbone of the even-chain diacid. Within each the odd-chain diacids, the $R_1$, $R_2$, $R_3$, and αβ within each two-carbon-subunit can be independent of (and so can be identical to or different from) the $R_1$, $R_2$, $R_3$, and αβ of every other two-carbon-subunit of the molecule.

In some embodiments, the present invention provides methods for making the odd-chain diacid malonic acid.

In some embodiments, the present invention provides methods for making the odd-chain diacid pimelic acid.

Malonic acid has numerous industrial uses. Malonate esters of alkyl chains from 1-20 carbons are used, for example, in the production of cosmetics, perfumes and fragrances, barbiturates, agrochemicals, preservatives, flavoring agents, non-steroidal anti-inflammatory agents (NSAIDS), anti-depression drugs, sedatives, anesthetics, hypnotics, anti-convulsants, and paint binders. Malonic acid is also used in chicken feed as an osteoresorptive inhibitor, as an electrolyte additive for metal anodization, to produce electroactive polymers, to produce methylidene malonates and polymers thereof, and in complex mixtures such as Santosol® DME-1. These complex mixtures can be use as fire retardants, UV protective films, hydrophilic polymers and films, hydrophobic polymers and films, binders, sealants, and anaerobic adhesives. Diesters of malonate also have numerous uses. For example, diethylmalonate is used in perfumes as well as in the synthesis of many compounds such as barbiturates, artificial flavorings, vitamin B1 and vitamin B6. Other diesters that can be produced in accordance with the methods of the invention include but are not limited to dimethyl malonate, dipropyl malonate, dibutyl malonate, and up to C20 alcohols esterified to malonate.

In some embodiments, the invention results in the production of a lactam. Such lactams can be comprised of C4-C16 of either even or odd chain length. Where the terms even and odd are used, they refer to the number of carbons in the backbone of the molecule.

By starting with the 4-carbon gamma amino butyric acid (GABA), as described below, even chain lactams C4 and higher, including but not limited to caprolactam and the C12 lactam used in engineering polymer Nylon 12, can be produced. By introducing a beta-alanine loading module, such as that from the fluvirucin pathway, biosynthetic pathways that produced odd chain lactams, such as that used in engineering polymer Nylon 11, can be generated.

In some embodiments of the invention, even chain lactams are biosynthesized by using a loading module derived from a glycine-specific NRPS module. More than a dozen such modules have been identified thus far in nature (see, e.g., Rausch, et al. *Nucleic Acids Research*, 2005, 33 (18):5799-5808). PKS/NRPS hybrids are common in nature and a number of these biosynthesis pathways have been shown to be amenable to engineering.

In some embodiments of the invention an alpha amino acid is incorporated by the PKS/NRPS hybrid system to yield a lactam possessing a pendent side chain. For example, if a phenylalanine loading module is used in a triketide system incorporating two malonyl-CoAs and catalyzing all three possible reductions with each extension, the output is a caprolactam derivative with a phenyl side chain. The same type of approach is used in accordance with the methods of the invention to produce derivatized lactams, the cognate open chain forms and diamines by appropriate selection of the NRPS loading module. With any of the described starters (loading modules), one also exploits the flexibility of PKS systems to generate derivatives with a great variety of different oxidative states and alkyl side chains. This flexibility applies not only to the systems starting with GABA, but those starting with any other amino acid.

In some embodiments of the invention the PKS or PKS/NRPS hybrid system produces the cognate amino acid to the described lactam. These acids can be accessed biologically by incorporating a thioesterase that releases the polyketide as a free acid or by chemical hydrolysis of the lactam ex vivo.

6-Aminocaproic acid is the cognate amino acid to caprolactam. It is used to treat excessive postoperative bleeding, especially after procedures in which a great amount of bleeding is indicated. It is marketed under the trade name Amicar®. It is produced by ring opening of caprolactam. A biological route for synthesis of 6-aminocaproic acid and, therefore, caprolactam, as provided by the invention, is advantageous.

In some embodiments of the invention the PKS or PKS/NRPS hybrid system produces a diamine. These compounds can be accessed biologically by incorporating a thioesterase and amino transferase that coordinately release and convert the final Acyl-ACP thioester to a terminal amine.

The present invention provides for a polyketide synthase (PKS) capable of synthesizing 7-keto-8-amino-pelargonic acid (KAPA). KAPA is an advance intermediate in biotin biosynthesis. Introducing an alternative route to KAPA circumvents a number of regulatory check points in the biosynthesis of biotin. Therefore, the addition of a novel KAPA biosynthesis pathway or KAPA itself, to biotin producing organism is a means to increasing production of this valuable chemical. The present invention provides for a recombinant nucleic acid that encodes a polyketide synthase (PKS) capable of synthesizing KAPA. The present invention provides for a host cell comprising any of the recombinant nucleic acid and/or PKS of the present invention, wherein when cultured under a suitable condition the host cell is capable of producing KAPA, and optionally biotin. The present invention provides a method of producing KAPA, and optionally biotin, comprising: providing a host cell of the present invention, and culturing said host cell in a suitable culture medium such that KAPA, and optionally biotin, is produced. The present invention provides for a composition comprising KAPA, and optionally biotin, isolated from a host cell from which KAPA, and optionally biotin, is produced, and trace residues and/or contaminants of the host cell.

7-Keto-8-amino-pelargonic acid (KAPA) has the following structure:

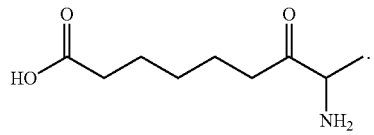

In some embodiments of the invention, the polyketide synthase (PKS) is capable of synthesizing an even-chain diacid and the PKS comprises two polypeptide modules, wherein the first module comprises an aspartate specific adenylation (A) domain, modified to load succinate instead of aspartate, from the non-ribosomal peptide synthetase (NRPS) pathway for calcium-dependent antibiotic (CDA) from *Saccharopolyspora erythraea* linked to a peptidylcarrier protein (PCP) domain and a second module comprising a PKS ketosynthase (KS) domain, wherein the PCP domain is capable of interacting with the KS domain. In some embodiments of the invention, the PCP domain is the PCP domain from the bleomycin pathway from *Streptomyces verticillus*. In some embodiments of the invention, the A domain is directly linked to the PCP domain. In some embodiments of the invention, the second module comprises the KS domain (derived from the bleomycin pathway fused to nystatin module 5, wherein the even-chain diacid produced is adipic acid (see Example 1 and FIG. 11). In some embodiments of the invention, the modification of the A domain comprises the conserved aspartate residue ("Asp235") changed to glutamine.

In some embodiments of the invention ery TE is used to release free acids from our hybrid PKS. In other embodiments this role is fulfilled by the thioesterase MonCII from the monensin pathway in *Streptomyces cinnamonensis*, or that from the spirangein PKS.

Figure 7:
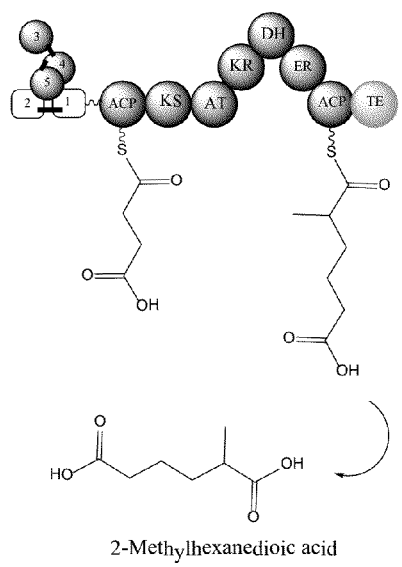
FIG. 7 shows: (A) replacement of the CoA ligase domain with a succinyl-CoA synthetase and (B) manipulation of the AT specificity of the extension domain.
Figure 7:
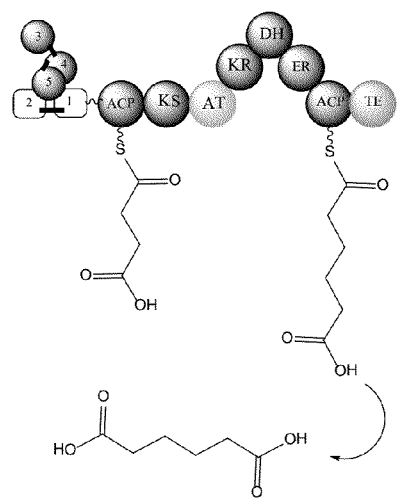

In some embodiments of the invention, the polyketide synthase (PKS) is capable of synthesizing an even-chain diacid and the PKS comprises the loading domain of the chondrochloren PKS wherein the CoA ligase domain of the loading domain is replaced with a succinyl-CoA synthetase, such the loading domain loads succinate instead of butyrate. In some embodiments, the AT specificity of the extender domain can also be changed. Two examples are shown in FIG. 7.

In some embodiments of the invention, the polyketide synthase (PKS) is capable of synthesizing an even-chain diacid and the PKS comprises a mutant non-ribosomal peptide synthetase (NRPS) domain mutated to incorporate succinate, instead of aspartate, is used. The mutant NRPS domain is produced by substituting the amino acid(s), including an Asp to Gln change at "Asp235" (the conserved Asp235 residue of the substrate-binding pocket as defined in the gramicidin S synthase phenylalanine-activating domain as identified by Challis G L, Ravel J, & Townsend C A. *Chem Biol.* 2000 Mar.; 7(3):211-24) a key residue involved in the recognition of the alpha nitrogen in an aspartate-specific A domain.

In some embodiments of the invention, the invention comprises extending and reducing a polyketide with a pendant carboxylate group.

Figure 8:
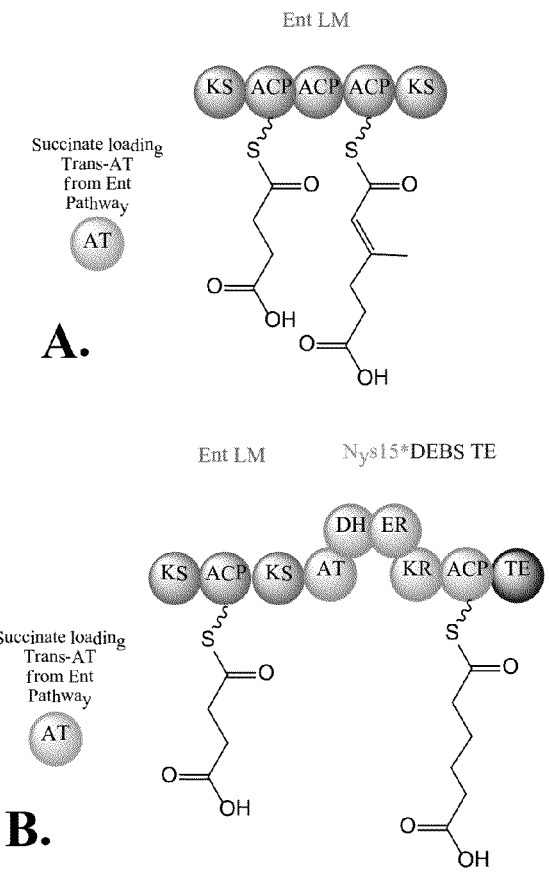
FIG. 8 shows: (A) the native chemistry of the etnangien loading module (Menche et al., J. Am. Chem. Soc. (2008) 130: 14234-14243; hereby incorporated by reference), and (B) the proposed truncation of this protein and fusion to a malonate-specific extender module and thioesterase hybrid PKS to yield adipic acid.

In some embodiments of the invention, the polyketide synthase (PKS) is capable of synthesizing an even-chain diacid and the PKS comprises a terminal module comprising Nystatin modules 5 or 15 or the like, which incorporate malonyl-CoA and fully reduce a corresponding β-carbonyl group, and an Ery TE domain fused to the terminal module. (See FIG. 8.)

In some embodiments of the invention, the polyketide synthase (PKS) is capable of synthesizing an even-chain diacid and the PKS comprises an etnangien loading module which incorporates succinate using a trans-AT domain. The etnangien loading module is taught in Menche et al. (*J. Am. Chem. Soc.* (2008) 130: 14234-14243; hereby incorporated by reference).

In some embodiments of the invention, the polyketide synthase (PKS) is capable of synthesizing an even-chain diacid and the PKS comprises a module in which a terminal carbon is incorporated as a methyl group which is later oxidized by a cytochrome P450. There are examples of methyl to carboxylate conversions in several of the amphipatic PKS pathways, such as for nystatin.

In some embodiments of the invention, the polyketide synthase (PKS) is capable of synthesizing an odd-chain diacid and the PKS comprises a mutant non-ribosomal peptide synthetase (NRPS) domain capable of loading succinic acid.

In some embodiments of the invention, the polyketide synthase (PKS) is capable of synthesizing lactam and the PKS comprises a non-ribosomal peptide synthetase (NRPS) domain capable of loading glycine.

In some embodiments of the invention, the polyketide synthase (PKS) is capable of synthesizing a diamine and the PKS comprises a non-ribosomal peptide synthetase (NRPS) domain capable of loading glycine.

In some embodiments of the invention, the polyketide synthase (PKS) is capable of synthesizing lactam and the PKS comprises a loading module capable of loading beta alanine.

Figure 9:
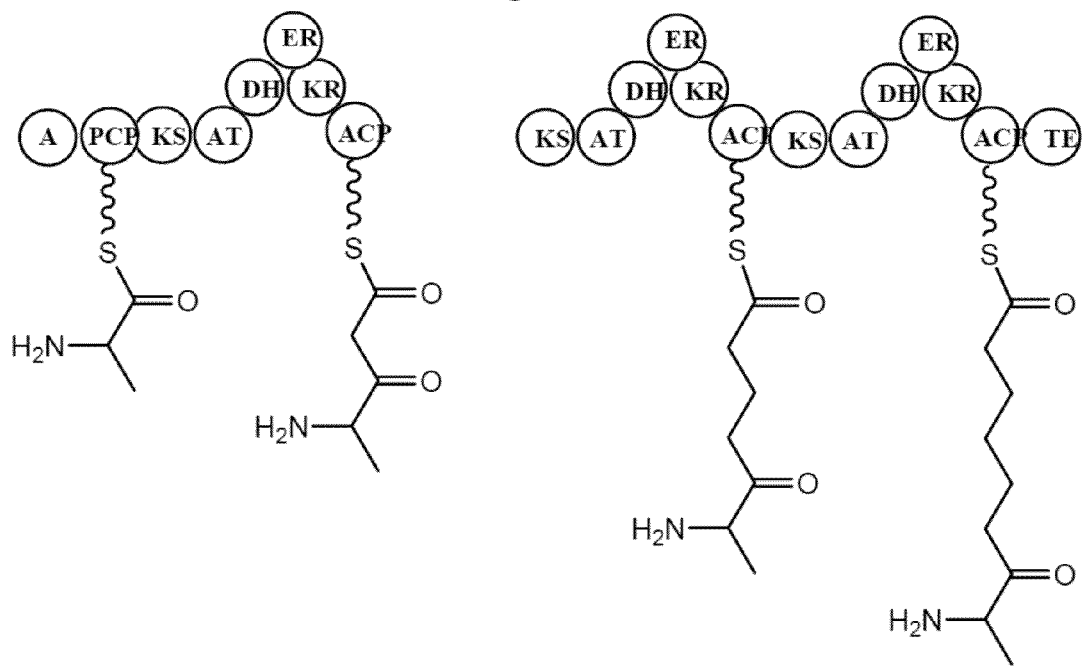
FIG. 9 shows the biosynthesis of 7-keto-8-amino-pelargonic acid (KAPA) using a NRPS-PKS hybrid of the present invention.

In some embodiments of the invention, the polyketide synthase (PKS) comprises a NRPS loading module specific for the amino acid alanine coupled to three PKS modules possessing all three reducing domains with a thioesterase (TE) at the C-terminus, wherein the PKS is capable of synthesizing 7-keto-8-amino-pelargonic acid (KAPA) (see FIG. 9).

Nucleic Acids Encoding the PKS

The present invention provides for a recombinant nucleic acid that encodes a polyketide synthase (PKS) of the present invention. The recombinant nucleic acid can be a double-stranded or single-stranded DNA, or RNA. The recombinant nucleic acid can encode an open reading frame (ORF) of the PKS of the present invention. The recombinant nucleic acid can also comprise promoter sequences for transcribing the ORF in a suitable host cell. The recombinant nucleic acid can also comprise sequences sufficient for having the recombinant nucleic acid stably replicate in a host cell. The recombinant nucleic acid can be replicon capable of stable maintenance in a host cell. In some embodiments, the replicon is stably integrated into a chromosome of the host cell. In some embodiments, the replicon is a plasmid. The present invention also provides for a vector or expression vector comprising a recombinant nucleic acid of the present invention. The present invention provides for a host cell comprising any of the recombinant nucleic acid and/or PKS of the present invention. In some embodiments, the host cell, when cultured under a suitable condition, is capable of producing the even-chain or odd-chain diacid, or lactam, or diamine.

The large number of polyketide pathways that have been elucidated provide many different options to produce diacids, lactams, and diamines as well as the large number of derivatives in accordance with the methods of the invention. While the products can be different in size and functionality, all employ the methods of the invention for biosynthesis. The interfaces between non-cognate enzyme partners can be determined for preparing the hybrid synthase. ACP-linker-KS and ACP-linker-TE regions from the proteins of interest are aligned to examine the least disruptive fusion point for the hybrid synthase. Genetic constructions will employ one of several standard sequence and ligation independent cloning method so as to eliminate the incorporation of genetic "scarring".

It will be apparent to one of skill in the art that a variety of recombinant vectors can be utilized in the practice of aspects of the invention. As used herein, "vector" refers to polynucleotide elements that are used to introduce recombinant nucleic acid into cells for either expression or replication. Selection and use of such vehicles is routine in the art. An "expression vector" includes vectors capable of expressing DNAs that are operatively linked with regulatory sequences, such as promoter regions. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those that integrate into the host cell genome.

The vectors may be chosen to contain control sequences operably linked to the resulting coding sequences in a manner that expression of the coding sequences may be effected in an appropriate host. Suitable control sequences include those that function in eukaryotic and prokaryotic host cells. If the cloning vectors employed to obtain PKS genes encoding derived PKS lack control sequences for expression operably linked to the encoding nucleotide sequences, the nucleotide sequences are inserted into appropriate expression vectors. This can be done individually, or using a pool of isolated encoding nucleotide sequences, which can be inserted into host vectors, the resulting vectors transformed or transfected into host cells, and the resulting cells plated out into individual colonies. Suitable control sequences for single cell cultures of various types of organisms are well known in the art. Control systems for expression in suitable host cells, such as yeast and prokaryotic host cells, are widely available and are routinely used. Control elements include promoters, optionally containing operator sequences, and other elements depending on the nature of the host, such as ribosome binding sites. Particularly useful promoters for prokaryotic hosts include those from PKS gene clusters that result in the production of polyketides as secondary metabolites, including those from Type I or aromatic (Type II) PKS gene clusters. Examples are act promoters, tcm promoters, spiramycin promoters, and the like. However, other bacterial promoters, such as those derived from sugar metabolizing enzymes, such as galactose, lactose (lac) and maltose, are also useful. Additional examples include promoters derived from biosynthetic enzymes such as for tryptophan (trp), the β-lactamase (bla), bacteriophage lambda PL, and T5. In addition, synthetic promoters, such as the tac promoter (U.S. Pat. No. 4,551,433; hereby incorporated by reference), can be used.

As noted, particularly useful control sequences are those which themselves, or with suitable regulatory systems, activate expression during transition from growth to stationary phase in the vegetative mycelium. Illustrative control sequences, vectors, and host cells of these types include the modified *S. coelicolor* CH999 and vectors described in PCT publication no. WO 96/40968 and similar strains of *S. lividans*. See U.S. Pat. Nos. 5,672,491; 5,830,750; 5,843,718; and 6,177,262, each of which is hereby incorporated by reference. Other regulatory sequences may also be desirable which allow for regulation of expression of the PKS sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes that confer antibiotic resistance or sensitivity to the plasmid.

The various PKS nucleotide sequences, or a mixture of such sequences, can be cloned into one or more recombinant vectors as individual cassettes, with separate control elements or under the control of a single promoter. The PKS subunits or components can include flanking restriction sites to allow for the easy deletion and insertion of other PKS subunits. The design of such restriction sites is known to those of skill in the art and can be accomplished using the techniques described above, such as site-directed mutagenesis and PCR. Methods for introducing the recombinant vectors of the present invention into suitable hosts are known to those of skill in the art and typically include the use of $CaCl_2$ or other agents, such as divalent cations, lipofection, DMSO, protoplast transformation, conjugation, and electroporation.

Host Cells Comprising the PKS

The present invention provides for a host cell comprising any of the recombinant nucleic acid and/or PKS of the present invention. In some embodiments, the host cell, when cultured, is capable of producing an even-chain or odd-chain diacid, or lactam, or diamine. The host cell can be a eukaryotic or a prokaryotic cell. Suitable eukaryotic cells include yeast cells, such as from the genus *Saccharomyces* or *Schizosaccharomyces*. A suitable species from the genus *Saccharomyces* is *Saccharomyces cerevisiae*. A suitable species from the genus *Schizosaccharomyces* is *Schizosaccharomyces pombe*. Suitable prokaryotic cells include *Escherichia coli, Bacillus* or *Streptomyces* species.

The PKS can be in a host cell, or isolated or purified. The PKS can synthesize the even-chain or odd-chain diacid, or lactam, or diamine in vivo (in a host cell) or in vitro (in a cell extract or where all necessary chemical components or starting materials are provided). The present invention provides methods of producing the even-chain or odd-chain diacid, or lactam, or diamine using any of these in vivo or in vitro means.

In some embodiments of the invention, the host cell comprises a PKS of the present invention capable of producing pimelic acid, and further comprises the enzymes pimelyl-CoA synthetase, 8-amino-7-oxononanoate synthase, 7,8-diamino-pelargonic acid (DAPA) synthase, dethiobiotin synthase, and biotin synthase, and/or one or more nucleic acids encoding pimelyl-CoA synthetase, 8-amino-7-oxononanoate synthase, DAPA synthase, dethiobiotin synthase, and biotin synthase, or functional variants thereof. When the host cell is cultured under a suitable condition, the host cell is capable of expressing or producing pimelyl-CoA synthetase, 8-amino-7-oxononanoate synthase, DAPA synthase, dethiobiotin synthase, and biotin synthase, or functional variants thereof, which in turn are capable of converting pimelic acid into biotin (or Vitamin H).

In some embodiments of the invention, the host cell comprises a PKS of the present invention capable of producing KAPA, and further comprises the enzymes 7,8-diamino-pelargonic acid (DAPA) synthase, dethiobiotin synthase, and biotin synthase, or functional variants thereof, and/or one or more nucleic acids encoding DAPA synthase, dethiobiotin synthase, and biotin synthase, or functional variants thereof. When the host cell is cultured under a suitable condition, the host cell is capable of expressing or producing DAPA synthase, dethiobiotin synthase, and biotin synthase, or functional variants thereof, which in turn are capable of converting KAPA into biotin (or Vitamin H).

Examples of suitable pimelyl-CoA synthetase are the gene products encoded by the bio W genes of *Bacillus subtilus*, and *Bacillus sphearicus*. An illustrative amino acid sequence, of *B. subtilus* pimelyl-CoA synthetase (GenBank Accession No.: AAC00261), comprises:

```
  1  mngshedggk hisggerlip fhemkhtvna llekglshsr gkpdfmqiqf eevhesikti 61  qplpvhtnev scpeegqkla rlllekegvs rdviekayeq ipewsdvrga vlfdihtgkr 121  mdqtkekgvr vsrmdwpdan fekwalhshv pahsrikeal alaskvsrhp avvaelcwsd 181  dpdyitgyva gkkmgyqrit amkeygteeg crvffidgsn dvntyihdle kqpiliewee 241  dhds (SEQ ID NO: 1)
```

Examples of suitable 8-amino-7-oxononanoate synthase are the gene products encoded by the bioF genes of *E. coli*, *B. subtilus*, and *B. sphearicus*. An illustrative amino acid sequence, of *E. coli* 8-amino-7-oxononanoate synthase (GenBank Accession No.: AP_001407), comprises:

```
  1  mswqekinaa ldarraadal rrrypvagga grwlvaddrq ylnfssndyl glshhpqiir
 61  awqqgaeqfg igsggsghvs gysvvhqale eelaewlgys rallfisgfa anqaviaamm
121  akedriaadr lshaslleaa slspsqlrrf ahndvthlar llaspcpgqq mvvtegvfsm
181  dgdsaplaei qqvtqqhngw lmvddahgtg vigeqgrgsc wlqkvkpell vvtfgkgfgv
241  sgaavlcsst vadyllqfar hliystsmpp aqaqalrasl avirsdegda rreklaalit
301  rfragvqdlp ftladscsai qplivgdnsr alqlaeklrq qgcwvtairp ptvpagtarl
361  rltltaahem qdidrllevl hgng (SEQ ID NO: 2)
```

Examples of suitable DAPA synthases are BIO3 of *S. cerevisae*, and the gene product encoded by the bioA genes of *E. coli*, *B. subtilus*, and *B. sphearicus*. An illustrative amino acid sequence, of *E. coli* DAPA synthase (GenBank Accession No.: AP_001405), comprises:

```
  1  mttddlafdq rhiwhpytsm tsplpvypvv saegcelils dgrrlvdgms swwaaihgyn
 61  hpqlnaamks qidamshvmf ggithapaie lcrklvamtp qplecvflad sgsvavevam
121  kmalqywqak gearqrfltf rngyhgdtfg amsvcdpdns mhslwkgylp enlfapapqs
181  rmdgewderd mvgfarlmaa hrheiaavii epivqgaggm rmyhpewlkr irkicdregi
241  lliadeiatg fgrtgklfac ehaeiapdil clgkaltggt mtlsatlttr evaetisnge
301  agcfmhgptf mgnplacaaa naslailesg dwqqqvadie vqlreqlapa rdaemvadvr
361  vlgaigvvet thpvnmaalq kffveqgvwi rpfgkliylm ppyiilpqql qrltaavnra
421  vqdetffcq (SEQ ID NO: 3)
```

Examples of suitable dethiobiotin synthases are BIO4 of *S. cerevisae*, and the gene product encoded by the bioD genes of *E. coli*, *B. subtilus*, and *B. sphearicus*. An illustrative amino acid sequence, of *E. coli* dethiobiotin synthase (GenBank Accession No.: CAA00967), comprises:

```
  1  mskryfvtgt dtevgktvas callqaakaa gyrtagykpv asgsektpeg lrnsdalalq
 61  rnsslqldya tvnpytfaep tsphiisaqe grpieslvms aglralehka dwvlvegagg
121  wftplsdtft fadwvtqeql pvilvvgvkl gcinhamlta qviqhagltl agwvandvtp
181  pgkrhaeymt tltrmipapl lgeipwlaen penaatgkyi nlall (SEQ ID NO: 4)
```

Examples of suitable biotin synthases are BIO2 of *S. cerevisae*, and the gene product encoded by the bioB genes of *E. coli*, *B. subtilus*, and *B. sphearicus*. An illustrative amino acid sequence, of *E. coli* biotin synthase (Gen Bank Accession No.: AP_001406), comprises:

```
  1  mahrprwtls qvtelfekpl ldllfeaqqv hrqhfdprqv qvstllsikt gacpedckyc 61  pqssryktgl eaerlmeveq vlesarkaka agstrfcmga awknpherdm pyleqmvqgv 121  kamgleacmt lgtlsesqaq rlanagldyy nhnldtspef ygniittrty qerldtlekv 181  rdagikvcsg givglgetvk draglllqla nlptppesvp inmlvkvkgt pladnddvda 241  fdfirtiava rimmptsyvr lsagreqmne qtqamcfmag ansifygckl lttpnpeedk 301  dlqlfrklgl npqqtavlag dneqqqrleq almtpdtdey ynaaal (SEQ ID NO: 5)
```

Methods of Using the PKS

The present invention provides a method of producing an even-chain or odd-chain diacid, or lactam, or diamine comprising: providing a host cell of the present invention, and culturing said host cell in a suitable culture medium such that the even-chain or odd-chain diacid, or lactam, or diamine is produced. The method can further comprise isolating said even-chain or odd-chain diacid, or lactam, or diamine from the host cell and the culture medium. The method can further comprise reacting the even-chain or odd-chain diacid with a diamine to produce a nylon. The method can also comprise the polymerization of the lactams, or cognate amino acids. A suitable diamine is an alkane diamine, such as hexane-1,6-diamine. Alternatively, the method can further comprise reacting the even-chain or odd-chain diacid with a dialcohol to produce a polyester. A suitable dialcohol is an alkane diol, such as ethylene glycol, propane diol, or butanediol. A variety of methods for heterologous expression of PKS genes and host cells suitable for expression of these genes and production of polyketides are described, for example, in U.S. Pat. Nos. 5,843,718; 5,830,750 and 6,262,340; WO 01/31035, WO 01/27306, and WO 02/068613; and U.S. Patent Application Pub. Nos. 20020192767 and 20020045220; hereby incorporated by reference.

The present invention provides for a composition comprising an even-chain or odd-chain diacid, or lactam, or diamine isolated from a host cell from which the even-chain or odd-chain diacid, or lactam, or diamine is produced, and trace residues and/or contaminants of the host cell. Such trace residues and/or contaminants include cellular material produced by the lysis of the host cell.

The even-chain diacids, such as adipic acid, or odd-chain diacids, or lactam, or diamine, provide for the production of "green" nylon, such as that used in Mohawk carpet fibers. Besides nylon production, the ability to manipulate the side chains of the even-chain or odd-chain diacids, or lactams, or diamines provides for the production of novel polymer precursors that would lead to polymers with a variety of properties. These products may also serve as adhesive, lubricants or precursors for pharmaceuticals or other more complicated compounds.

Producing Biotin

The present invention provides for a method of producing biotin, comprising: providing a host cell comprising one or more nucleic acids encoding and capable of expressing or producing a PKS capable of producing pimelic acid, and pimelyl-CoA synthetase, 8-amino-7-oxononanoate synthase, DAPA synthase, dethiobiotin synthase, and biotin synthase, and culturing said host cell in a suitable culture medium such that biotin is produced. A variety of methods for heterologous expression of these genes and host cells suitable for expression of these genes and production of polyketides are described herein. A hybrid PKS capable of producing pimelic acid is taught in U.S. Patent Application Ser. No. 61/040,583, PCT International Patent Application PCT/US2009/038831, and U.S. patent application Ser. No. 12/922,204, which are incorporated by reference.

The present invention provides for a method of producing biotin, comprising: providing a host cell comprising one or more nucleic acids encoding and capable of expressing or producing a PKS capable of producing KAPA, and DAPA synthase, dethiobiotin synthase, and biotin synthase, and culturing said host cell in a suitable culture medium such that biotin is produced. A variety of methods for heterologous expression of these genes and host cells suitable for expression of these genes and production of polyketides are described herein.

The method can further comprise isolating said biotin from the host cell and the culture medium. The method can further comprise administering the isolated biotin to a human or animal in need of or suspected to be in need of biotin. In some embodiments, the administering comprises the human or animal orally ingesting the biotin.

The present invention provides for a composition comprising biotin isolated from a host cell from which the biotin is produced, and trace residues and/or contaminants of the host cell. Such trace residues and/or contaminants include cellular material produced by the lysis of the host cell. The biotin isolated is useful for nutritional purposes. The type and amount of the trace residues and/or contaminants isolated with the biotin is not harmful to the health of a human or animal orally ingesting the biotin.

The present invention has one or more of the following advantages: (1) it reduces the dependence on oil for producing certain chemicals, and (2) it serves as a means of capture and sequestration of carbon from the atmosphere.

The invention having been described, the following examples are offered to illustrate the subject invention by way of illustration, not by way of limitation.

In the examples below, reference is made to either DNA or protein sequence present in the NCBI data that is used to produce the enzymes required to make the products described. It is understood that the protein sequences can be back-translated to produce DNA segments of preferred codon usage, or that the DNA sequences present in databases can be used directly or changed to correspond to the same protein sequence with preferred codon usage.

EXAMPLE 1

Production of Adipic Acid Using a Mutated NRPS A Domain

Figure 11:
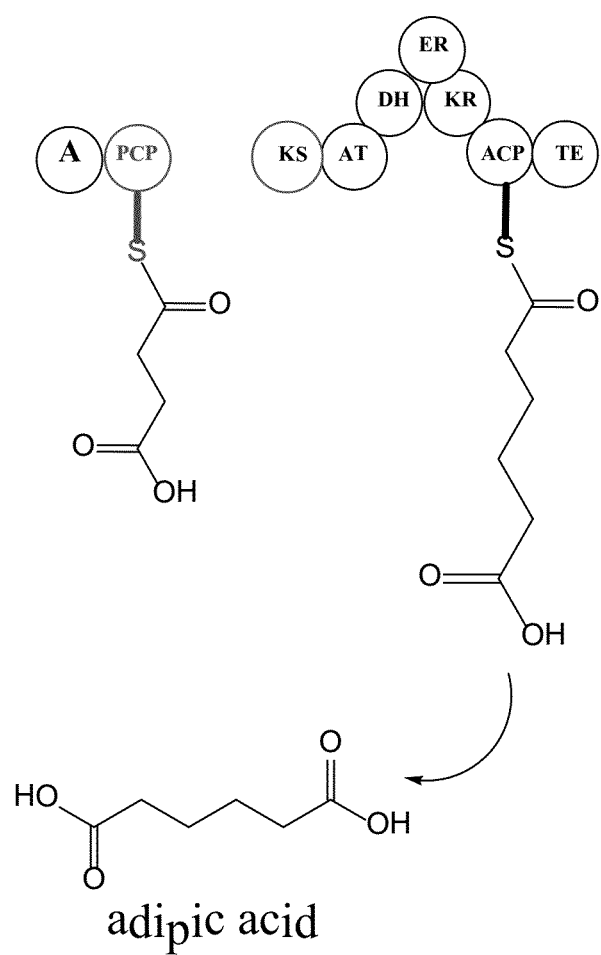
FIG. 11 shows the model for the PKS/NRPS hybrid system described in Example 1.

The production of adipic acid is achieved by coupling an aspartate specific A domain from the non-ribosomal peptide synthetase (NRPS) pathway for calcium-dependent antibiotic (CDA) from *Saccharopolyspora erythraea* to a peptidyl-carrier protein (PCP) domain from bleomycin pathway from *Streptomyces verticillus*. This PCP is chosen because it natively interacts with a PKS ketosynthase (KS) domain. The chimeric protein is designated AAS1 (adipic acid synthase ORF 1). As a second ORF (aas2), this KS domain (bleomycin PKS) is fused to nystatin module 5 which was previously fused to the thioesterase (TE) domain from the erythromycin pathway. The two enzymes and their catalytic domains are illustrated in FIG. 11. In order to change the specificity of the adenylation domain from the CDA pathway, the amino acid loading domain is mutated at a conserved aspartate residue ("Asp235") that is known to stabilize the alpha-amino side chain of the natively loaded amino acid. By blocking this interaction we sought to change the specificity from aspartate to the des-amino form of the same molecule, succinate. A saturation mutagenesis library is made at this position of the A domain. Each of the 20 versions of this enzyme were carried on the backbone pBbA7c and were co-transformed into *E. coli* BAP-1, grown to a sufficient optical density (OD), such as ~0.4, induced and analyzed by LC-MS. The construct carrying an Asp to Gln mutation at "Asp235" showed adipic acid production (Table 2).

TABLE 2

Samples labeled UI are uninduced, those labeled are induced cultures. I9 was lost. UI6 carries an Asp to Gln mutation at "Asp235".

| Sample name | Area | uM | mg/L |
|---|---|---|---|
| UI 1 | 0 | 0 | 0 |
| UI 2 | 0 | 0 | 0 |
| UI 3 | 0 | 0 | 0 |
| UI 4 | 0 | 0 | 0 |
| UI 5 | 0 | 0 | 0 |
| UI 6 | 42,671 | 1.56 | 0.23 |
| UI 7 | 0 | 0 | 0 |
| UI 8 | 0 | 0 | 0 |
| UI 9 | 0 | 0 | 0 |
| UI 10 | 0 | 0 | 0 |
| UI 11 | 0 | 0 | 0 |
| UI 12 | 0 | 0 | 0 |
| UI 13 | 0 | 0 | 0 |
| UI 14 | 0 | 0 | 0 |
| UI 15 | 0 | 0 | 0 |
| UI 16 | 0 | 0 | 0 |
| UI 17 | 0 | 0 | 0 |
| UI 18 | 0 | 0 | 0 |
| UI 19 | 0 | 0 | 0 |
| UI 20 | 0 | 0 | 0 |
| I 1 | 0 | 0 | 0 |
| I 2 | 0 | 0 | 0 |
| I 3 | 0 | 0 | 0 |
| I 4 | 0 | 0 | 0 |
| I 5 | 0 | 0 | 0 |
| I 6 | 0 | 0 | 0 |
| I 7 | 0 | 0 | 0 |
| I 8 | 0 | 0 | 0 |
| I 9 | 0 | 0 | 0 |
| I 10 | 0 | 0 | 0 |
| I 11 | 0 | 0 | 0 |
| I 12 | 0 | 0 | 0 |
| I 13 | 0 | 0 | 0 |
| I 14 | 0 | 0 | 0 |
| I 15 | 0 | 0 | 0 |
| I 16 | 0 | 0 | 0 |
| I 17 | 0 | 0 | 0 |
| I 18 | 0 | 0 | 0 |
| I 19 | 0 | 0 | 0 |
| I 20 | 0 | 0 | 0 |

EXAMPLE 2

Production of Even-chain Diacids Using the Spirofungin Biosynthesis Genes

Figure 12:
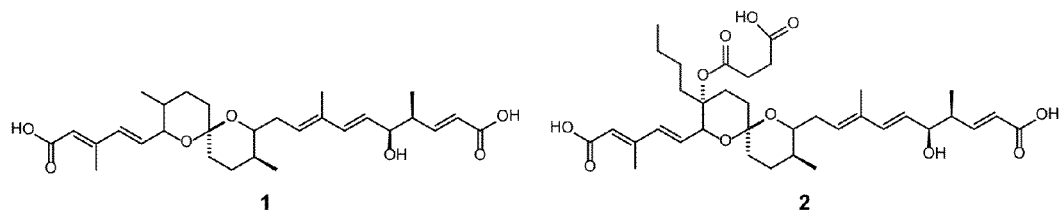
FIG. 12 shows spirofungin A [16-1] is a dicarboxylic acid composed of twenty-four carbons in its polyketide backbone that is organized into a spiroketal sub-structure. It is produced by the bacterium Streptomyces violaceusniger Tü 4113. Reveromycin [16-2], produced from Streptomyces sp. SN-593 has a similar backbone and spiroketal substructure but differs from spirofungin in the atoms shown in blue.

Spirofungin A (FIG. 12-1) is a dicarboxylic acid composed of twenty-four carbons in its polyketide backbone that is organized into a spiroketal sub-structure. It is produced by the bacterium *Streptomyces violaceusniger* Tü 4113. Reveromycin (FIG. 12-2), produced from *Streptomyces* sp. SN-593 has a similar backbone and spiroketal substructure but differs from spirofungin in the atoms shown in blue.

Figure 13:
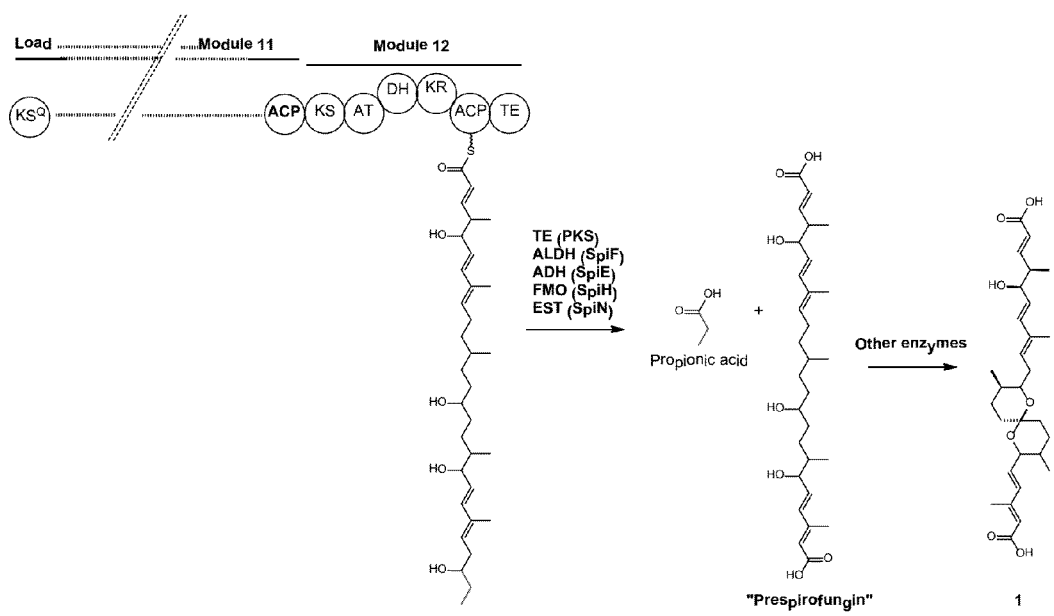
FIG. 13 shows a pathway to convert the final PKS-bound acyl intermediate to spirofungin.

Sequencing of the corresponding genes involved in the biosynthesis of the two compounds indicated that the polyketide is produced with a 27-carbon backbone by a type I polyketide synthase and then subsequently released and processed into the 24-carbon atom backbone containing an acid group at each end. Through analysis and comparison of the sequences of the genes flanking the PKS in both organisms, we have identified the pathway for the production of that converts the final acyl-ACP intermediate of spirofungin in module 12 of the spirofungin PKS to spirofungin A (FIG. 13).

The PKS consists of 12 modules and determines the biosynthesis of an acyl intermediate with 27 carbons in its chain. As shown in FIG. 13, the acyl chain contains an OH group at C-25 (C-1 is attached to the S atom covalently associated with the ACP domain). The thioesterse (TE) domain of module 12 releases the acyl chain either as a free acid at C-1 or as a 26-member macrolactone which is formed between C-1 and the OH at C25. This compound is then converted to the free intermediate designated "prespirofungin" through the action of the following enzymes: (1) An esterase (EST) that opens the lactone. The gene determining the esterase activity is designated ORF1 in the spirofungin cluster. (2) An alcohol dehydrogenase-like enzyme (ADH) that converts the 25-OH to its corresponding ketone. ADH is determined by ORF7 in the spirofungin cluster. (3) A flavin-binding family monooxygenase (FMO) that attacks C24, breaking the C24-C25 bond releasing the free acid (prespirofungin) and propionaldehyde. FMO is determined by ORF4. (4) An aldehyde dehydrogenase (ALDH) that converts propionaldehyde to propionic acid. ALDH is determined by ORF6. Prespirofungin is converted to spirofungin A through the action of additional enzymes determined by genes in the spirofungin biosynthesis cluster that form the spiroketal sub-structure.

It is possible that the spiroketal sub-structure is formed before the acyl end is converted to the acidic group, either while the acyl chain is tethered to the ACP of module 12, or immediately after it is released by the thioesterase (and opened from its macrolactam structure by the esterase (SpiN). The acid group is then formed by the action of SpiE, SpiH, and SpiF as described above. Similarly, the acid group at C24 of reveromycin is formed by the action of similar enzymes EST (RevN), ADH (RevE), FMO (RevH), and ALDH (RevF).

Figure 14:
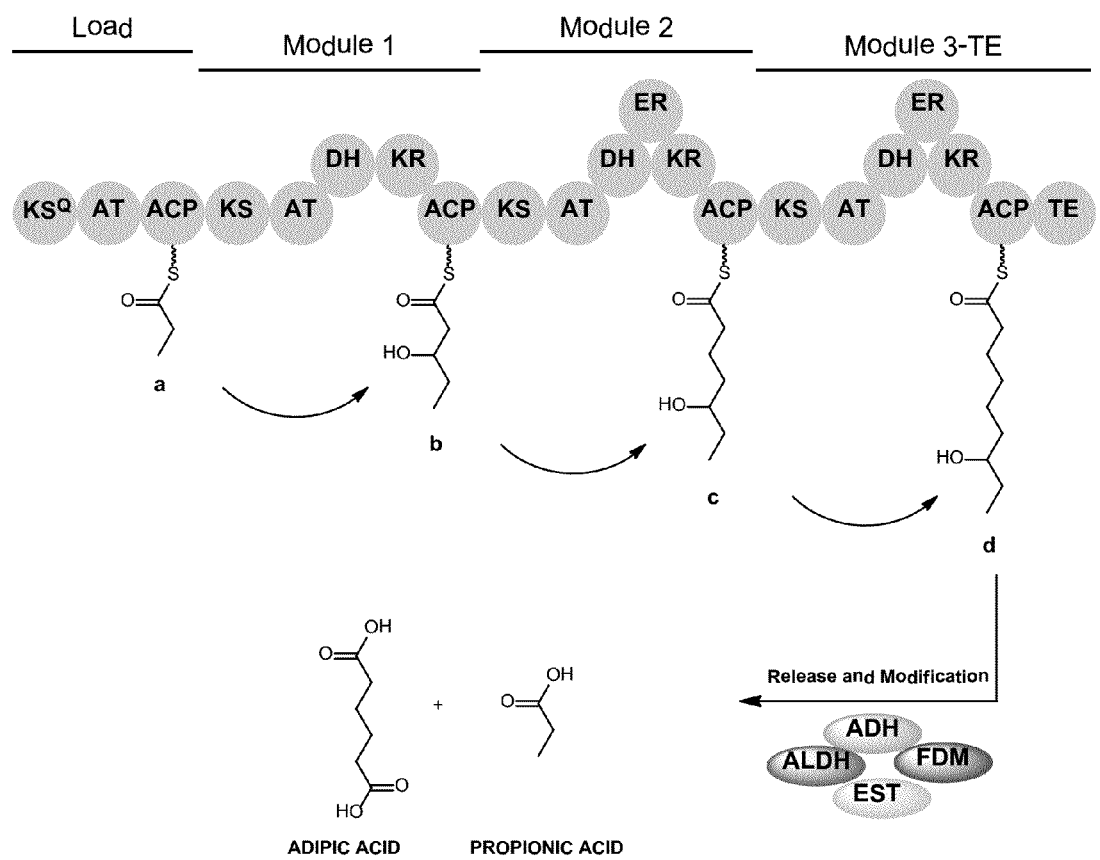
FIG. 14 shows the composition of the PKS and biochemical scheme for the production of adipic acid in accordance with an embodiment of the invention.

An approach to produce adipic acid is shown in FIG. 14. The PKS is composed of a loading module and three extension modules with the domains indicated. The PKS produces the intermediates [a], [b], [c] and [d], each attached to the ACP domain at the end of the biochemical processes in the load module and modules 1-3, respectively. Compound d consists of a 9-carbon backbone that is released from the ACP by the TE domain and converted to the 6-carbon diacid, adipic acid, and propionic acid by the action of the enzymes EST, ADH, FMO and ALDH, which are produced from expression of the genes spiN, spiE, spiH, and spiF from the spirofungin gene cluster from *Streptomyces violaceusniger* Tü 4113 (see, the www site ncbi.nlm.nih.gov/nuccore/CP002994.1: Spirofungin cluster: Strvi_6572-Strvi_6584), or the corresponding genes revN, revE, revH, and revF from the reveromycin gene cluster from *Streptomyces* sp. SN-593 (NCBI Accession No. AB568601).

EXAMPLE 3

Production of Even-chain Diacids Using the Succinyl CoA Ligase

Figure 4:
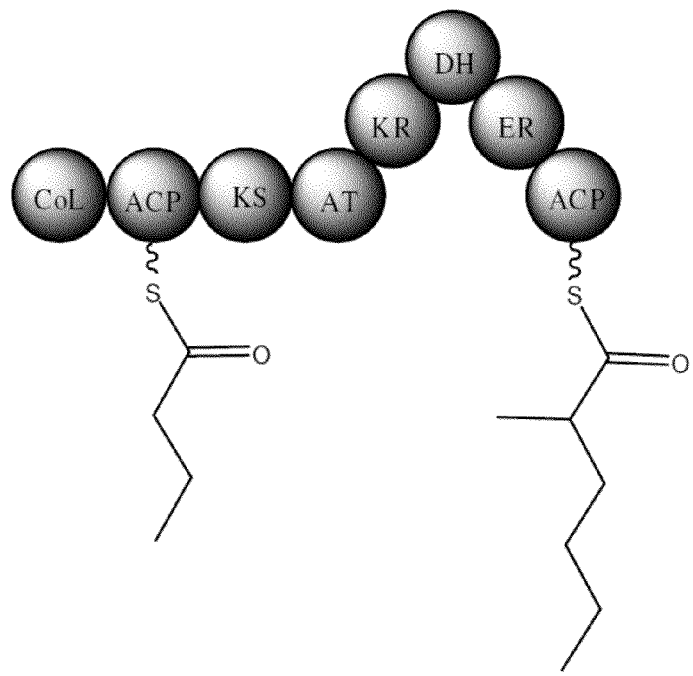
FIG. 4 shows the native loading and $1^{st}$ extension of the chondrochlorens PKS as catalyzed by CndA.
Figure 5:
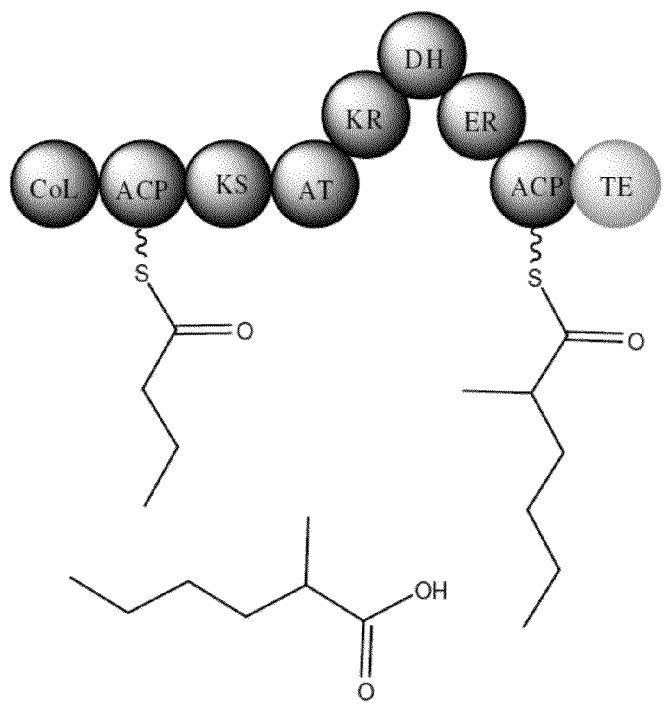
FIG. 5 shows the addition of a thioesterase domain resulting in the release of the free acid product.
Figure 10:
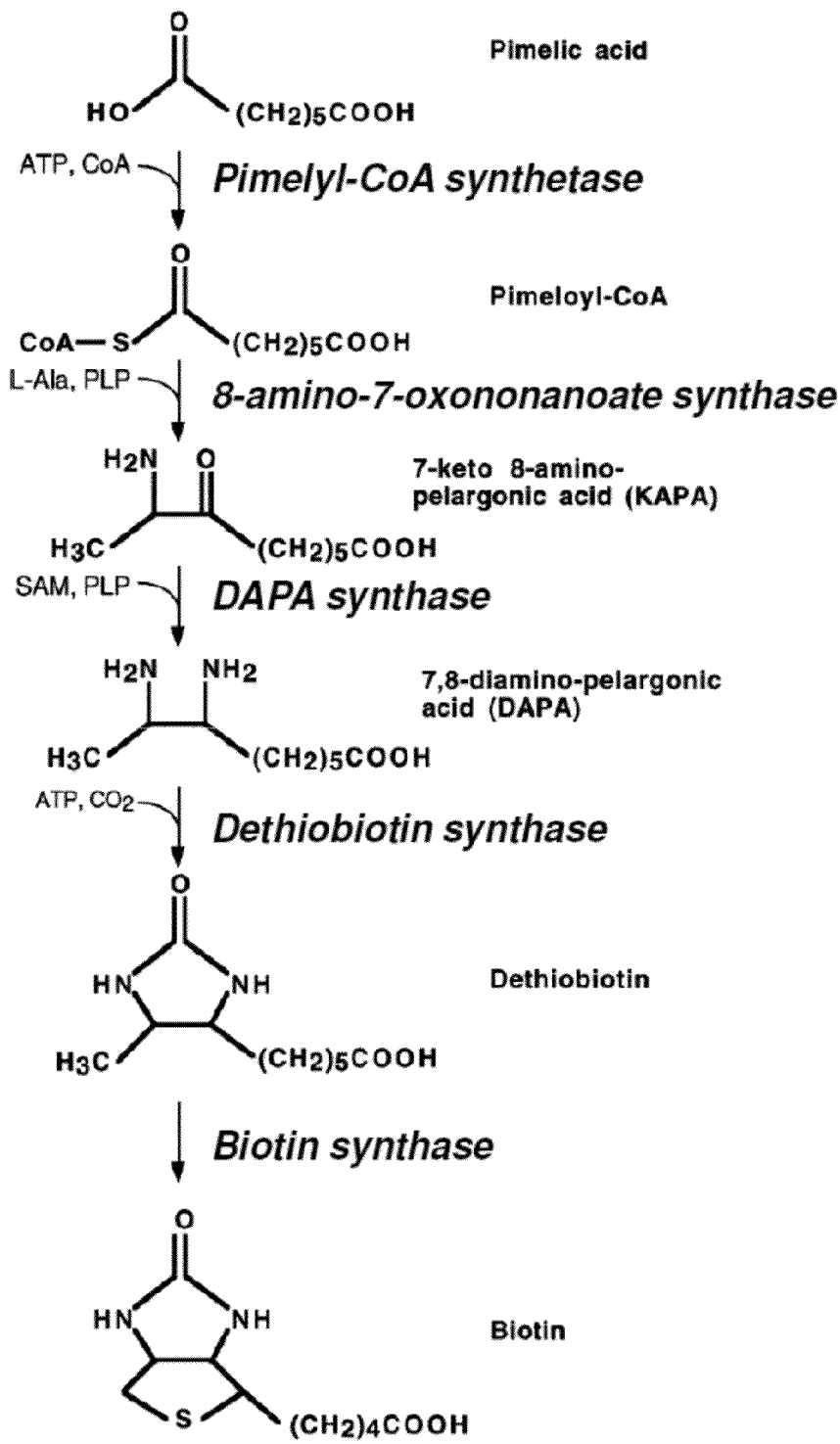
FIG. 10 shows the pathway from which pimelic acid and/or KAPA is converted into biotin (or Vitamin H).

Succinyl CoA Ligase. The recent publication of the chondrochloren biosynthesis cluster shows a loading domain that consists of a CoA ligase and ACP domain (Rachid et al., "Unusual chemistry in the biosynthesis of the antibiotic chondrochlorens," Biology & Chemistry 16:70-81, 2009; hereby incorporated by reference). The native system loads a four-carbon butyrate, extends with methylmalonate and fully reduces the β-carbonyl (FIG. 4). The addition of a thioesterase domain (DEBS-TE) catalyzes the release of 2-methylhexanoic acid (FIG. 10).

Figure 6:
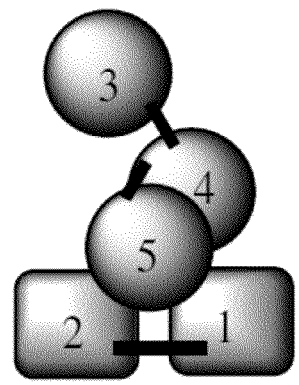
FIG. 6 shows a model of the E. coli succinyl-CoA synthetase.

Replacement of the CoA ligase domain with a succinyl-CoA synthetase allows the loading of succinate. There are a number of succinyl-CoA ligases. All appear to function as heterodimers or α2β2 tetramers. They all carry the 5 conserved domains illustrated in FIG. 6. Because we desire to load succinate onto the phosphopantetheinyl arm of the ACP rather than the phosphopantetheinyl arm of CoA, we should be able to eliminate domain 1. An adhesion domain could be added to the N-terminus of the ACP and another to part of the succinyl-CoA synthetase complex. These would be co-expressed with a scaffold protein to link them together. The obvious question lies in the placement of the adhesion on the CoA-synthetase. This will have to be done in such a way that the active site is oriented toward the phosphopantetheinyl arm of the ACP.

This combined with the addition of the TE domain would facilitate the production of 2-methyl-hexanedioic acid (FIG. 7A). Finally, the native CndA enzyme loads a methylmalonate extender unit. One can change the AT specificity (which has been done successfully via targeted mutagenesis of a few residues) or couple the loading domain to a module containing a malonate loading AT and all three reducing domains, such as Nys-mod5. The result in introducing all of these modifications would be a minimal PKS system that produces adipic acid (FIG. 7B).

EXAMPLE 4

Production of Even-chain Diacids Using the Etnangien Loading Module

Figure 15:
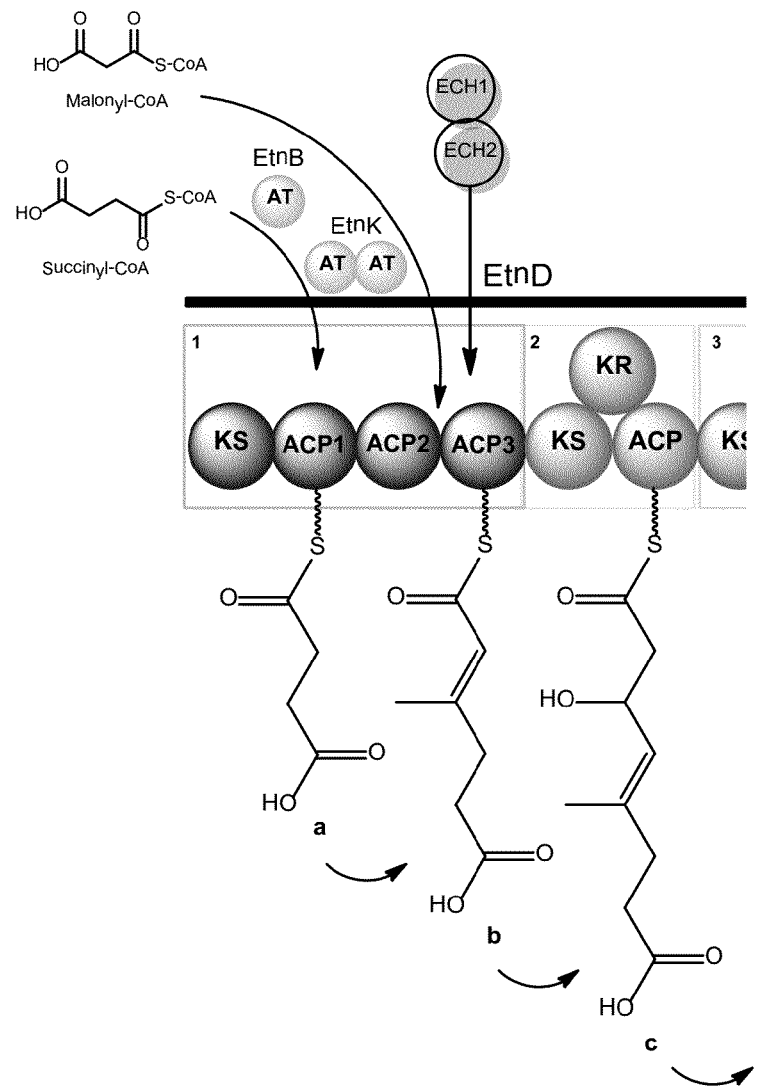
FIG. 15 shows the early steps in the biosynthesis of etnangien.

Etnangien is a macrolide-polyene antibiotic produced from *Sorangium cellulosum* that is composed of a macrocylic ring and a long polyketide chain that terminates with a carboxylate group. The beginning steps of the biosynthesis of the etnangien is shown in FIG. 15. Succinyl-CoA is loaded on the ACP1 domain of module 1 using a discrete (trans) AT enzyme encoded by EtnB or EtnK to produce succinyl-ACP (FIG. 15[a]) Similarly, malonyl-CoA is loaded on ACP2 or ACP3 of module 1 by EtnB or EtnK (malonyl-ACP not shown). The KS domain of module 1 creates thethioester intermediate 3-oxo-5-carboxypentanoyl-ACP (not shown). The 3-oxo group is then attacked by a β-methylation enzyme system, ECH1 and ECH2 that adds a methyl group at C-3 and leaves the 2,3-bond unsaturated resulting in intermediate 3-methyl-5-carboxy-[2,3]pentenoyl-ACP (FIG. 15[b]). This acyl-intermediate is used for the next round of polyketide synthesis to yield compound c (FIG. 15[c]).

Figure 16:
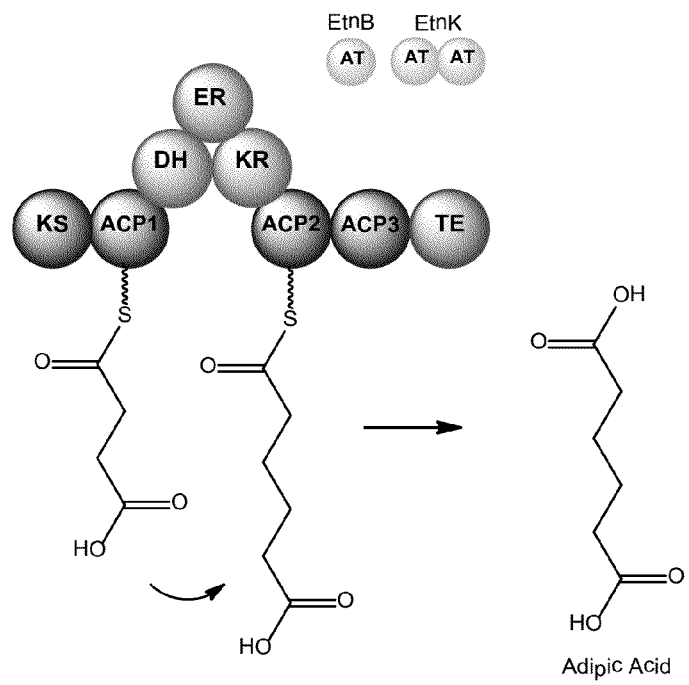
FIG. 16 shows the biosynthesis of adipic acid employing module 1 of the etnangien PKS in accordance with an embodiment of the invention.

Production of Adipic Acid—Two strategies are used to produce adipic acid employing components of the etnangien PKS. In the first, (FIG. 16), a chimeric PKS employs the segment of the etnangien PKS in the gene etnD containing the entire sequence of module 1 from *Sorangium cellulosum* (NCBI Accession No. YP001613827), and a segment from a second PKS that encodes the DH-ER-KR domains introduced between the ACP2 and ACP3. These domains are available as a contiguous segment from numerous PKSs, including but not limited to module 4 of the erythromycin PKS from *Saccharopolyspora erythraea* (NCBI Accession No. M63677.1), module 4 of the pikromycin PKS from *Streptomyces venezuelae* (NCBI Accession No. BD232534.1), or modules 7 or 12 of the oligomycin PKS from *Streptomyces avermitilis* (NCBI Accession No. NC_003155). The genes for EtnB and EtnK from *Sorangium cellulosum* (NCBI Accession Nos. YP001613825 and YP001613834, respectively) are also introduced into the host to produce the corresponding trans AT enzymes to ensure that both succinyl-ACP1 and malonyl-ACP2 are formed. The KS domain acts to form the 6 carbon diketide that is then reduced to adipyl-ACP by the KR, DH and ER domains and released by the TE domain to yield adipic acid. Examples of TE domains include, but are not limited to, the TE domain from the niddamycin PKS from *Streptomyces caelestis* (NCBI Accession No. AF016585), the oligomycin PKS from *Streptomyces avermitilis* (NCBI Accession No. NC_003155), the epothilone PKS from *Sorangium cellulosum* (NCBI Accession No. AF217189), the pikromycin PKS from *Streptomyces venezuelae* (NCBI Accession No. BD232534), and the erythromycin PKS from *Saccharopolyspora erythraea* (NCBI Accession No. M63677.1).

Figure 17:
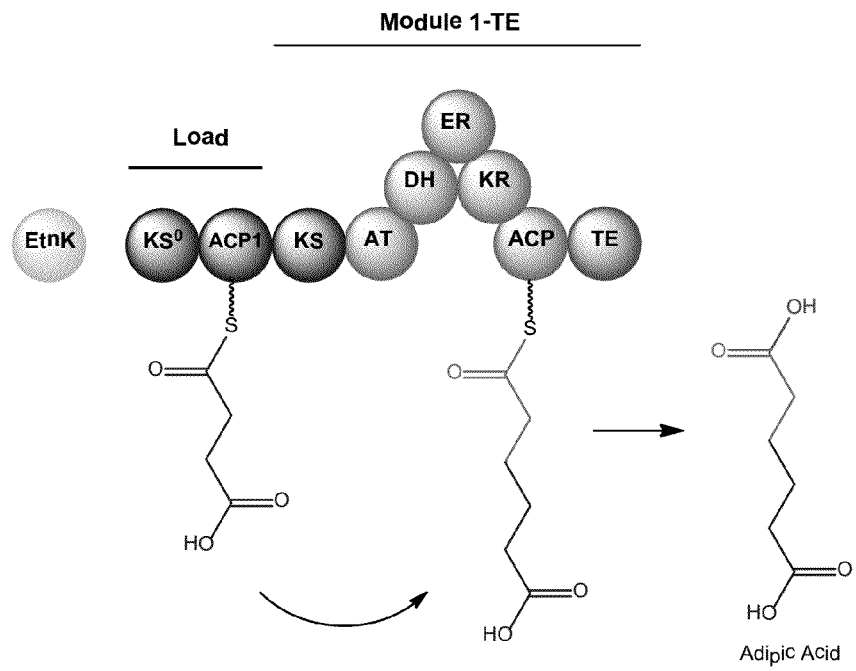
FIG. 17 shows the biosynthesis of adipic acid employing module 1 of the etnangien PKS in another embodiment of the invention.

In a second embodiment employing the etnangien PKS components, a chimeric PKS is constructed as a single ORF employing, as shown in FIG. 17, DNA segments corresponding to the inactivated KS and ACP1 domains from module 1 of EtnD linked to the KS domain of module 2 from *Sorangium cellulosum* (NCBI Accession No. YP001613287) linked to a DNA segment containing malonyl-specific AT domain and the DH-ER-KR-ACP domains linked to a TE domain. Inactivation of the KS domain is accomplished by deleting all or most of the KS domain without disrupting the reading frame. Examples of AT-DH-ER-KR-ACP segments that can be used in this construct include, but are not limited to the AT-DH-ER-KR-ACP segments from module 3 of the oligomycin PKS from *Streptomyces avermitilis* (NCBI Accession No. NC_003155), or modules 5 or 15 of the nystatin PKS from *Streptomyces noursei* (NCBI Accession No. AF263912). Examples of TE domains include, but are not limited to, the TE domain from the niddamycin PKS from *Streptomyces caelestis* (NCBI Accession No. AF016585), the oligomycin PKS from *Streptomyces avermitilis* (NCBI Accession No. NC 003155), the epothilone PKS from *Sorangium cellulosum* (NCBI Accession No. AF217189), the pikromycin PKS from *Streptomyces venezuelae* (NCBI Accession No. BD232534.1), and the erythromycin PKS from *Saccharopolyspora erythraea* (NCBI Accession No. M63677.1).

EXAMPLE 5

Employing an AMP-ligase-PCP Didomain as the Loading Module

The scheme for production of adipic acid employing an AMP ligase-PCP didomain to load succinic acid directly to the PKS is shown in FIG. 11. The A domain is a variant of the protein DhbE from *Bacillus subtilis* (NCBI Accession No. NP_391078). DhbE normally transfers dihydroxybenzoic acid to its cognate PCP, DhbB (NCBI Accession No. NP_391077). In the construct shown in FIG. 11, the Load Module consists of the A domain which is composed of DhbE*, a variant of DbhE containing the following amino acid substitutions: S240G, V329A, and V337K, and the PCP domain consisting of amino acids 188-312 of DhbB. The KS domain of module 1 is the KS domain of the borrelidin PKS from *Streptomyces parvulus* (NCBI Accession No. ABS90475). The AT-TE segment of the PKS is as shown in FIG. 17. Examples of AT-DH-ER-KR-ACP segments that can be used in this construct include, but are not limited to the AT-DH-ER-KR-ACP segments from module 3 of the oligomycin PKS from *Streptomyces avermitilis* (NCBI Accession No. NC_003155), or modules 5 or 15 of the nystatin PKS from *Streptomyces noursei* (NCBI Accession No. AF263912). Examples of TE domains include, but are not limited to, the TE domain from the niddamycin PKS from *Streptomyces caelestis* (NCBI Accession No. AF016585), the oligomycin PKS from *Streptomyces avermitilis* (NCBI Accession No. NC_003155), the epothilone PKS from *Sorangium cellulosum* (NCBI Accession No. AF217189), the pikromycin PKS from *Streptomyces venezuelae* (NCBI Accession No. BD232534.1), and the erythromycin PKS from *Saccharopolyspora erythraea* (NCBI Accession No. M63677.1).

EXAMPLE 6

Production of Malonic Acid Using PKS

Figure 18:
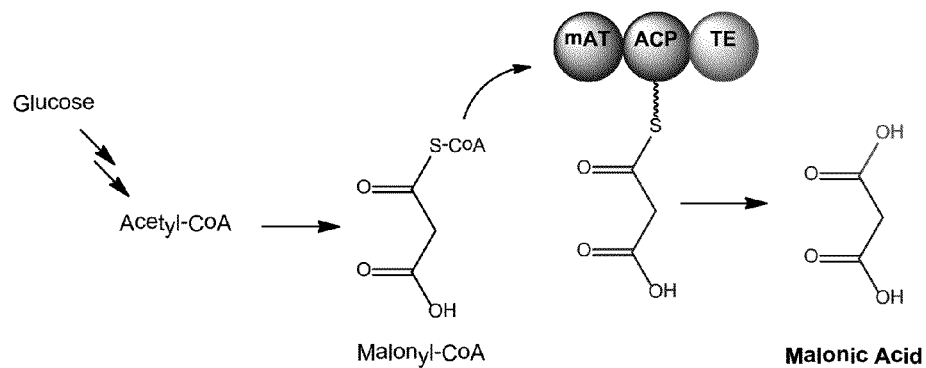
FIG. 18 shows the pathway of glucose to malonic acid employing a three domain chimeric PKS module in accordance with an embodiment of the invention.

As shown in FIG. 18, a single, three domain, chimeric PKS module that has a malonyl-specific acyltransferase (mAT) domain linked to its cognate ACP domain linked to a type I thioesterase (TE) domain will bind malonyl-CoA and release malonic acid. Malonyl-CoA is naturally present in all hosts, and is the substrate for the biosynthesis of fatty acids in prokaryotes and fatty acids and cholesterol or its analogs (e.g. ergosterol) in eukaryotes. Malonyl-CoA is readily produced from acetyl-CoA which is the primary degradation product of glucose metabolism. High titers of intracellular malonyl-CoA has been achieved in both prokaryotes and eukaryotes.

Numerous PKS load modules contain the cognate mAT-ACP didomains. Examples include, but are not limited to, the AT-ACP didomain from the load module from the chalcomycin PKS from *Streptomyces bikiniensis* (NCBI Accession No. AY509120), the niddamycin PKS from *Streptomyces caelestis* (NCBI Accession No. AF016585), the oligomycin PKS from *Streptomyces avermitilis* (NCBI Accession No. NC_003155), and the epothilone PKS from *Sorangium cellulosum* (NCBI Accession No. AF217189). Numerous PKSs also each contain a TE domain, any of which can be used in the assembly of the chimeric PKS herein. Examples include, but are not limited to, the TE domain from the niddamycin PKS from *Streptomyces caelestis* (NCBI Accession No. AF016585), the oligomycin PKS from *Streptomyces avermitilis* (NCBI Accession No. NC_003155), the epothilone PKS from *Sorangium cellulosum* (NCBI Accession No. AF217189), the pikromycin PKS from *Streptomyces venezuelae* (NCBI Accession No. BD232534.1), and the erythromycin PKS from *Saccharopolyspora erythraea* (NCBI Accession No. M63677.1). The mAT-ACP didomain or the TE domain can be cloned from the corresponding host organism or synthesized de novo employing the preferred codon usage for the ultimate malonic acid production host. The sequences separating the TE domain from its adjacent ACP domain in numerous PKSs is well understood, hence it is possible to synthesize de novo, or assemble from disparate sources, the complete mAT-ACP-TE chimeric module.

EXAMPLE 7

Production of Malonic Acid Using PKS+TEII

Figure 19:
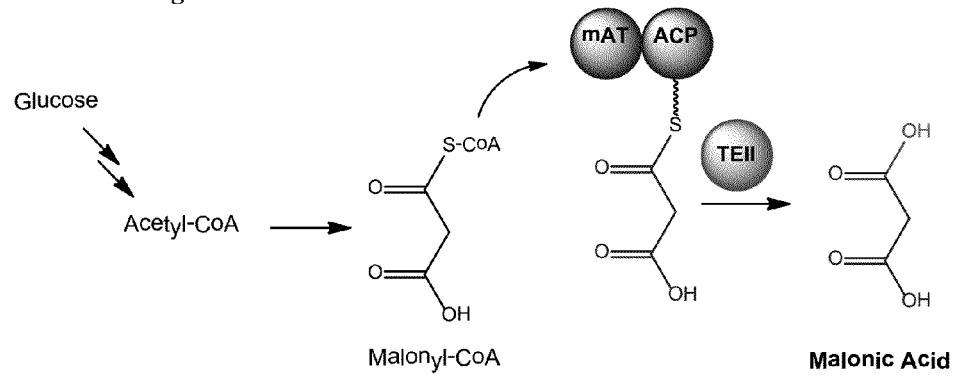
FIG. 19 shows the pathway of glucose to malonic acid employing a didomain PKS module and a type II thioesterase in accordance with an embodiment of the invention.

In this embodiment, the PKS module consists of a mAT-ACP didomain that loads malonyl-CoA and a separate type II thioesterase (TEII) that is specific for removing the CoASH moiety from short chain acyl-CoA thioesters to produce short chain acids (FIG. 19). Examples of mAT-ACP didomains include, but are not limited to, the AT-ACP didomain from the load module from the spiramycin, carbomycin, niddamycin, oligomycin, or epothilone PKS. The DNA segments encoding these didomains can be cloned from their respective natural hosts, or synthesized de novo employing employing preferred codon usage to enhance expression in the organism chosen for malonic acid production.

Examples of TEII enzymes include TEII proteins from genes involved in the biosynthesis of known polyketides, including, but not limited to, EryH from *Saccharopolyspora erythraea* (NCBI Accession No. M54983.1), MegH from *Micromonospora megalomiceae* (NCBI Accession No. AF2623245.1), GrsT from *Streptomyces bikiniensis* (NCBI Accession No. AY509120.1), or MonCII from *Streptomyces cinnamonensis* (NCBI Accession No. AF440781.1), from gene clusters involved in the biosynthesis of erythromycin, megalomicin, chalcomycin, and monensin, respectively. Other examples of TEII enzymes include the family of TesB-like enzymes from a variety of Gram-negative bacteria including, but not limited to, *Escherichia coli* (NCBI Accession No. ZP_003256460.1), *Shigella flexneri* (NCBI Accession No. NP_706346.2), *Salmonella enterica* (NCBI Accession No. ZP_02656512.1), or *Klebsiella pneumonia* (NCBI Accession No. ZP_06015648.1), or Gram positive bacteria including, but not limited to, *Brucella abortus* (NCBI Accession No. YP222547.1), *Agrobacterium tumefaciens* (NCBI Accession No. EGP58265.1), *Brevibacterium linens* (NCBI Accession No. ZP05914544.1), or *Micrococcus luteus* (NCBI Accession No. YP0029570745.1). The corresponding genes can be cloned from their native hosts or synthesized de novo employing preferred codon usage to enhance expression in the organism chosen for malonic acid production.

In this embodiment, the mAT-ACP didomain and TEII would be expressed as separate proteins either as part of an operon driven from a single promoter, or driven from separate promoters from either a single plasmid, two plasmids, a plasmid and the chromosome or from the chromosome exclusively. To enhance the overall rate of release of malonyl-CoA from the mAT-ACP didomain, genes for two or more TEII enzymes can be co-expressed in the host expressing the gene for the mAT-ACP didomain.

EXAMPLE 8

Production of Malonic Acid Using Trans-AT PKS

Figure 20:
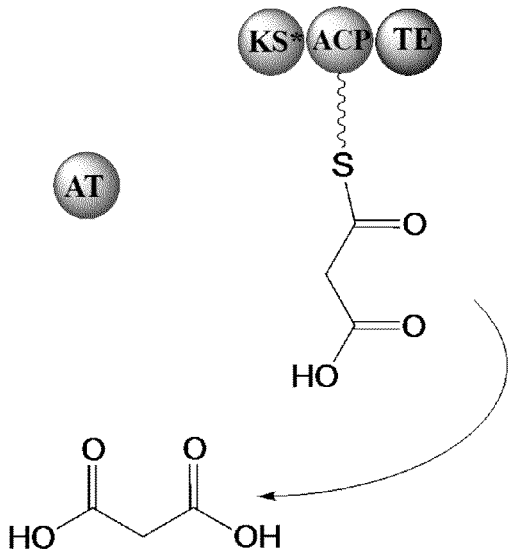
FIG. 20 shows the pathway of glucose to malonic acid employing a trans-AT PKS module and the associated AT protein in accordance with an embodiment of the invention. The KS* indicates that this domain is catalytically inactive, but included for structural reasons.

In another embodiment of this invention, the malonate producing PKS utilizes a "trans AT" PKS system (FIG. 20). Because all known trans AT PKSs utilize malonate, any of these ACPs can be coupled to a TE, so long as the upstream portions of the PKS responsible for dimerization and trans-AT recognition are retained. Example PKS sources for these domains are the mupirocin, bryostatin, leinamycin, and onnamide pathways. A thioesterase suitable for releasing a free carboxylate from the ACP thioester can be utilized in this system. Examples include the DEBS, spirangein, and kalamanticin PKSs. The KS* pictured in FIG. 20 indicates that this domain is catalytically inactive, but included for structural reasons.

EXAMPLE 9

Production of Caprolactam Using a PKS

Biosynthesis of caprolactam requires the synthesis of an amino-containing molecule that can start the biosynthesis of a polyketide chain on a PKS system. In the embodiment shown in FIG. 21, the starter is 4-aminobutyryl-CoA which is produced from the commonly available amino acid L-arigininine by enzymes designated Orf28, Orf33 and Orf27 from *Streptomyces aizunensis* (NCBI Accession No. AAX98201, AAX98208, AAX98202, respectively). Production of the pathway from arginine to 4-aminobutyryl-CoA is accomplished through the synthesis of DNA segments with the preferred codon usage corresponding to the protein sequences of Orf26, Orf33, and Orf27 from. 4-Aminobutyryl-CoA is transferred to the Load ACP domain of the PKS shown in FIG. 21 by the trans AT (Orf18) from *Streptomyces aizunensis* (NCBI Accession No. AAX98193) to yield the intermediate 4-aminobutyryl-ACP [a]. Intermediate a is extended by the PKS module 1 to produce the intermediate 6-aminohexanoyl-ACP [b]. The KS domain of module 1 corresponds to the KS domain of module 1 of the linearmycin PKS and is, hence, the natural domain that interacts with the Load ACP protein and to which the starting 4-aminobutyryl moiety is transferred during native linearmycin biosynthesis. The Load ACP through KS1 domain comes from the linearmycin PKS from *Streptomyces aizunensis* (NCBI Accession No. AAX98191). The mAT-DH-ER-KR-ACP segment of module I of FIG. 21 can be taken from a number of PKS systems. Examples include, but are not limited to the mAT-DH-ER-KR-ACP containing segment from module 22 of the linearmycin PKS from *Streptomyces aizunensis*, (NCBI database Accession No. AAX98191), module 3 of the oligomycin PKS from *Streptomyces avermitilis* (NCBI Accession No. NC_003155), or modules 5 or 15 of the nystatin PKS from *Streptomyces noursei* (NCBI Accession No. AF263912). Preferred TE domains shown in FIG. 21 that both releases and cyclizes intermediate b to caprolactam include, but are not limited to, the TE domain from the vicenistatin PKS from *Streptomyces halstedii* (NCBI Accession No. BAD08360), the leinamycin PKS from *Streptomyces atroolivaceus* (NCBI Accession No. AF484556), the salinilactam PKS from *Salinospora tropica* (NCBI Accession No. YP_001159601), and the BE-14106 PKS from *Streptomyces* sp. DSM 21069 (NCBI Accession No. FJ872523).

Figure 21:
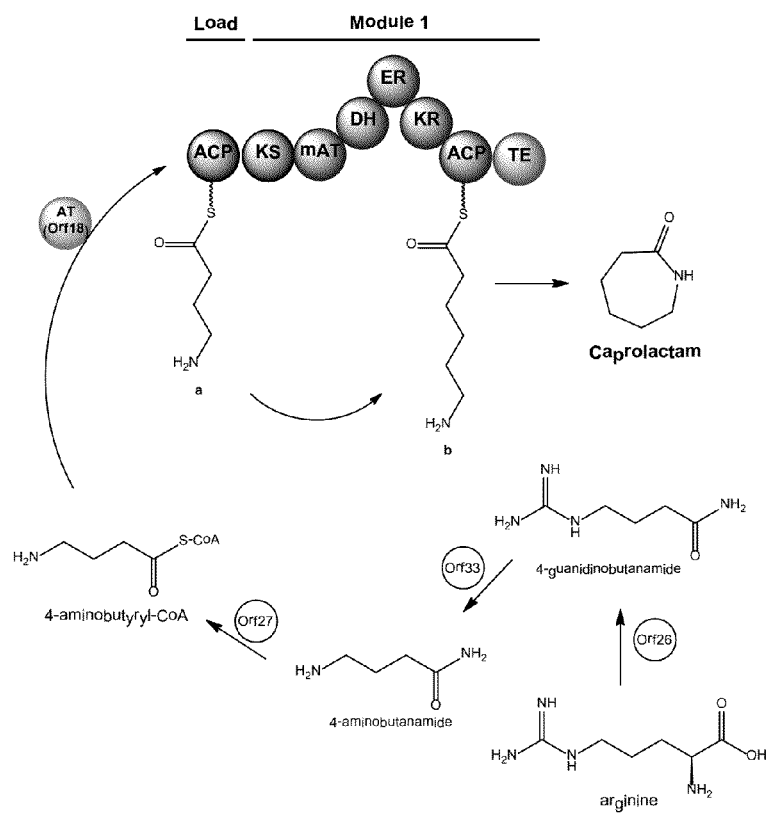
FIG. 21 shows a scheme for the biosynthesis of caprolactam.

Load ACP and KS1 domains are on separate proteins in the native system. The PKS shown in FIG. 21 is synthesized so that this precise arrangement is maintained, hence the PKS is composed of two separate proteins that interact to produce caprolactam.

EXAMPLE 10

Production of the GABA Starter Unit

Figure 22:
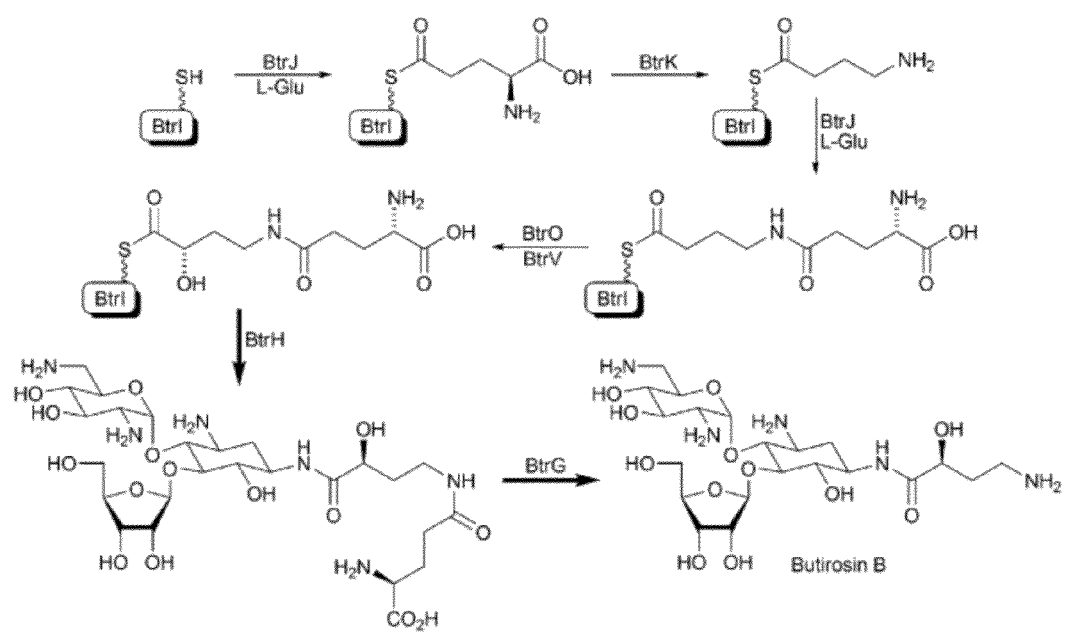
FIG. 22 shows the biosynthetic pathway of the HABA side chain of butirosin.

Butirosin is an aminoglycoside antibiotic that contains a 2-hydroxy-4-aminobutyric (HABA) side chain attached to the N1 of the central sugar, 2-deoxystreptamine. The pathway for synthesis of HABA is shown in FIG. 22. The enzyme BtrJ is a biotin-dependent carboxytransferase that transfers L-glutamic acid to BtrI, a stand-alone acyl carrier protein (ACP) creating the thioester. This is acted upon by the enzyme BtrK, a decarboxylase that produces 4-aminobutyryl-BtrI ([gamma-amino butyratyl] GABA-ACP). The remainder of the pathway is shown in FIG. 22.

Figure 23:
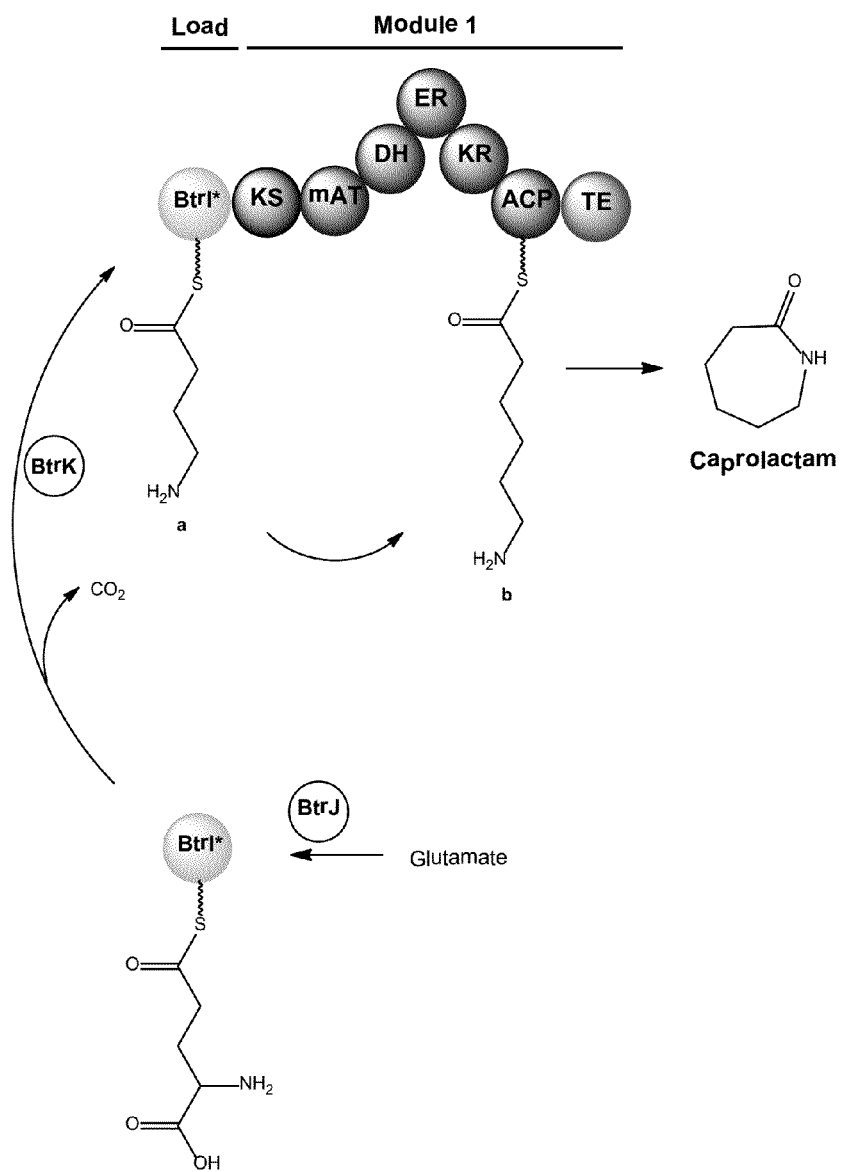
FIG. 23 shows a scheme for the biosynthesis of caprolactam in accordance, with an embodiment of the invention.

BtrI, BtrJ, and BtrK from *Bacillus circulars* (NCBI Accession Nos. BAE 07073, BAE07074, and BAE07075, respectively), is synthesized de novo employing the preferred codon usage for the host of choice. BtrI is altered to create BtrI* to contain the docking domain to allow it to interact with the KS domain of the PKS shown in FIG. 23. The KS-TE segment of module 1 is identical to that described in FIG. 21. In the instant scheme, a glutamyl-BtrI* thioester is formed through the action of BtrJ. The glutamyl moiety is then decarboxylated by BtrK to produce the load ACP of the PKS acylated with the 4-aminobutyryl starter [a]. As in the system shown in FIG. 21, this is converted to intermediate b and subsequently released and cyclized to caprolactam.

EXAMPLE 11

Production of Caprolactam Using a PKS

Figure 24:
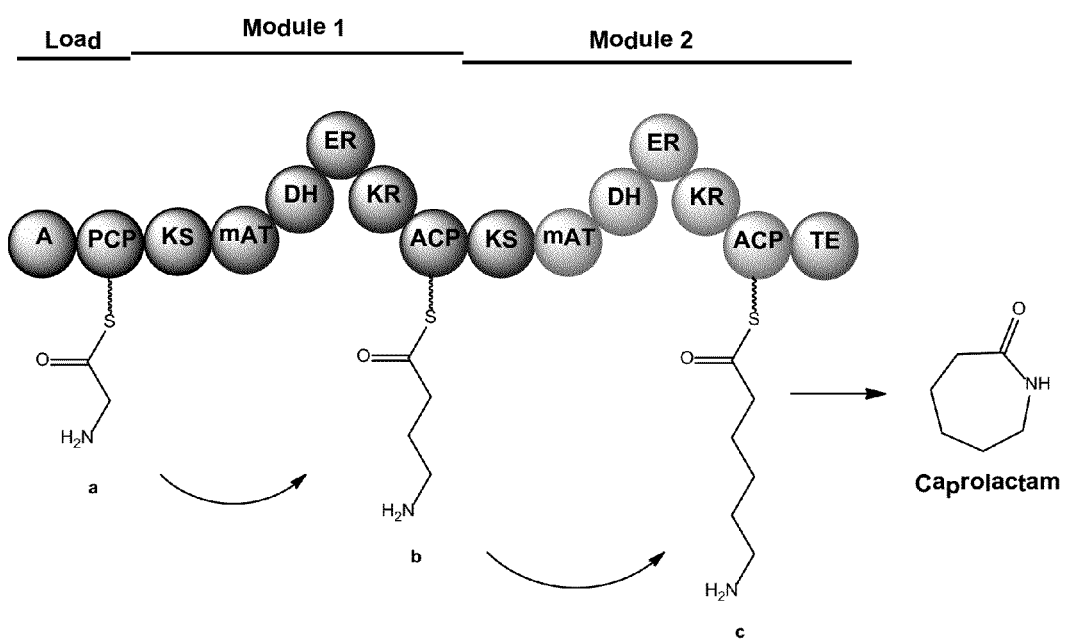
FIG. 24 shows a scheme for the biosynthesis of caprolactam in accordance with an embodiment of the invention.

A scheme for the biosynthesis of caprolactam is shown in FIG. 24. The load module is composed of a segment containing the A domain and PCP domain from module 7 of the oxazolomycin PKS. The A domain is specific for loading glycine to the adjacent PCP domain. The KS domain of module 1 is the KS domain of module 8 of the oxozolomycin PKS. The ACP-KS1 segment of the PKS shown in FIG. 24 is taken from the oxozolomycin PKS from *Streptomyces albus* (NCBI Accession No. ABS90475. This segment is fused to a segment containing the remaining AT-DH-ER-KR-ACP domains of module 2 and a full KS-AT-DH-ER-KR-ACP-TE-containing module 3. The entire PKS is produced as a single ORF. The AT1-KS2 segment can be taken from a number of PKS modules that contain a malonyl-specific AT domain and the DH-ER-KR-ACP and adjacent downstream KS domain including, but not limited to the AT-KS segment from AT5 through KS6 segment of the spirofungin PKS (Accession: *Streptomyces violaceusniger* Tü 4113 (www site ncbi.nlm.nih.gov/nuccore/CP002994.1: Spirofungin cluster: Strvi_6572-Strvi_6584), or the AT5-ACP5 segment from the reveromycin gene cluster *Streptomyces* sp. SN-593 (NCBI Accession No. AB568601), or the AT6-KS6, or AT15-KS 16 segments of the nystatin PKS from *Streptomyces noursei* (NCBI Accession No. AF263912). To avoid the possibility of intra modular recombination, the AT-ACP segments of modules 2 and 3 are not from the same native modules. Preferred TE domains shown in FIG. 24 that both releases and cyclizes intermediate b to caprolactam include, but are not limited to, the TE domain from the vicenistatin PKS from *Streptomyces halstedii* (NCBI Accession No. BAD08360), the leinamycin PKS from *Streptomyces atroolivaceus* (NCBI Accession No. AF484556), the salinilactam PKS from *Salinospora tropica* (NCBI Accession No. YP_001159601), and the BE-14106 PKS from *Streptomyces* sp. DSM 21069 (NCBI Accession No. FJ872523).

EXAMPLE 12

Production of 6-Aminocaproic Acid Using a PKS

Figure 25:
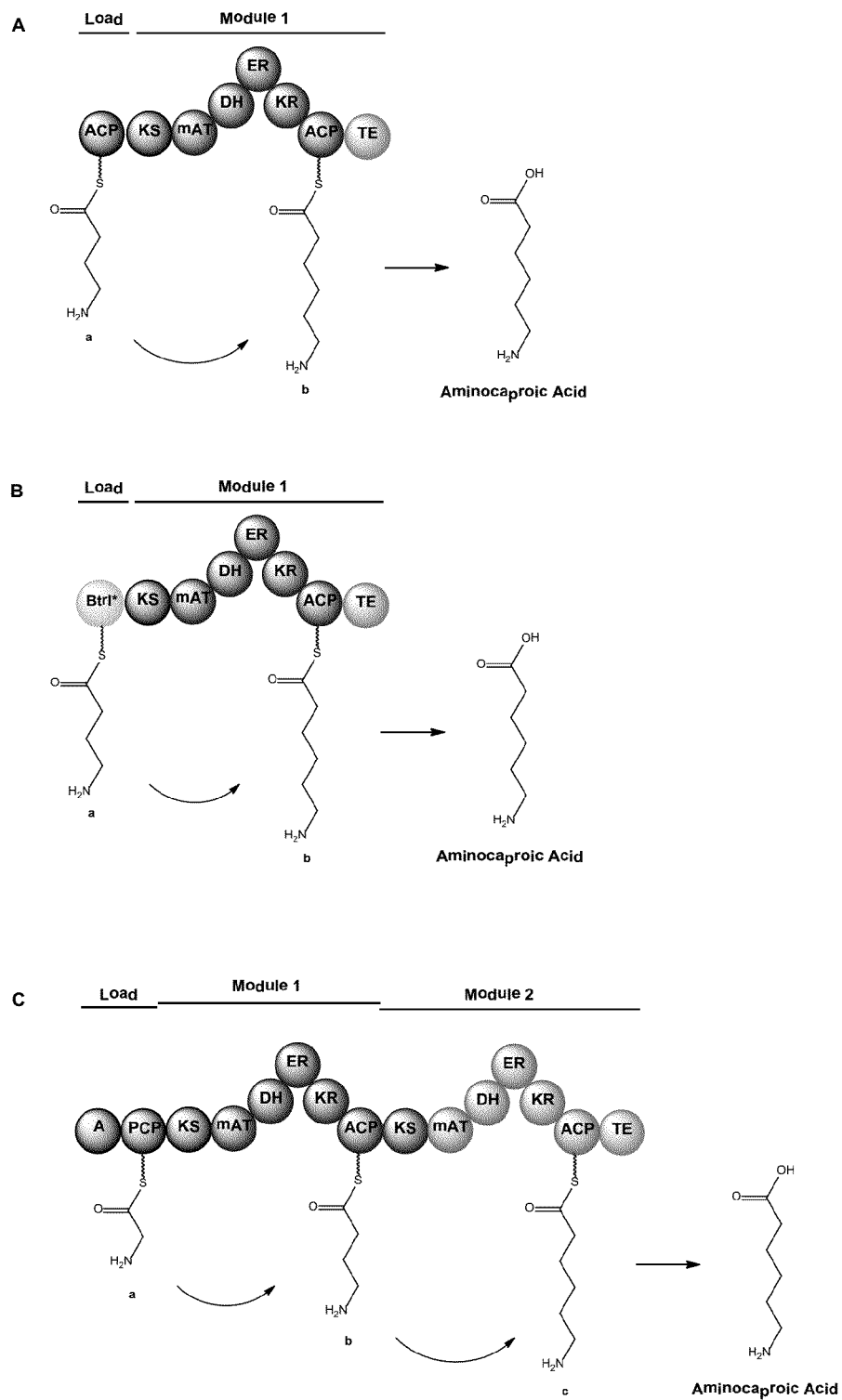
FIG. 25A-25C shows schemes for the biosynthesis of 6-aminocaproic acid in accordance with an embodiment of the invention.

Three schemes for the biosynthesis pathway of 6-aminocaproic acid are shown in FIG. 25 A-C. Schemes A, B, C are use the identical PKS elements and additional enzymes to produce intermediate a to the schems shown in FIGS. 22, 23, and 24, respectively, with the exception that the TE domain for the production of caprolactam is replaced with a TE domain that releases but does not cyclize intermediate b. Examples of such TE domains include, but are not limited to TE domains from the niddamycin PKS from *Streptomyces caelestis* (NCBI Accession No. AF016585), the oligomycin PKS from *Streptomyces avermitilis* (NCBI Accession No. NC_003155), the epothilone PKS from *Sorangium cellulosum* (NCBI Accession No. AF217189), the pikromycin PKS from *Streptomyces venezuelae* (NCBI Accession No. BD232534.1), and the erythromycin PKS from *Saccharopolyspora erythraea* (NCBI Accession No. M63677.1).

EXAMPLE 13

Production of 1,6-hexanediamine Using a PKS

Figure 26:
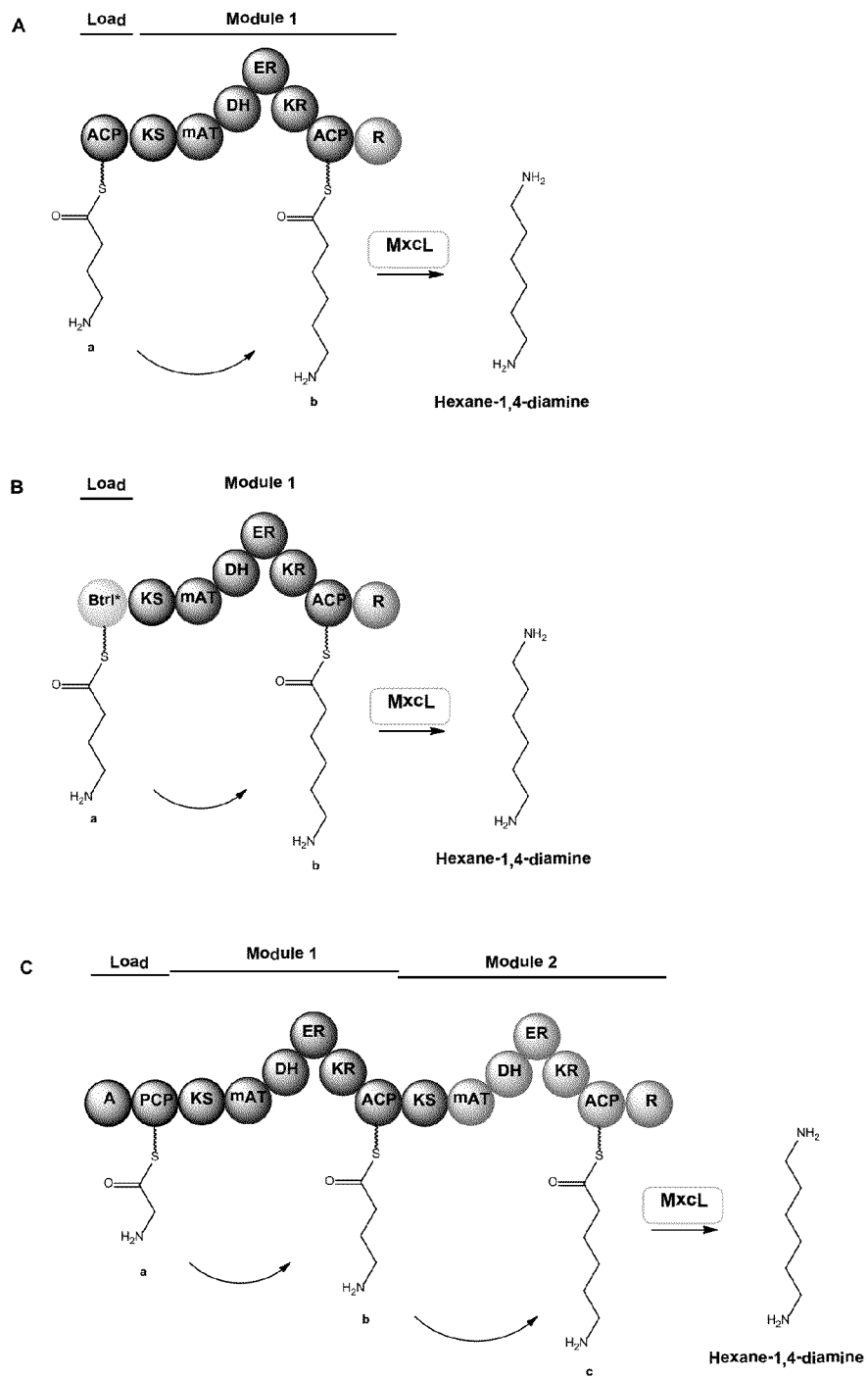
FIG. 26A-26C shows a scheme for the biosynthesis of hexane-1,4-diamine in accordance with an embodiment of the invention.

Three schemes for the biosynthesis pathway of hexane-1, 4-diamine are shown in FIG. 26 A-C. Schemes A, B, C are use the identical PKS elements and additional enzymes to produce intermediate a to the schemes shown in FIGS. 22, 23, and 24, respectively, with the exception that the TE domain for the production of caprolactam is replaced with the R domain from MxcG from *Stigmatella aurantiaca* (NCBI Accession No. AAG31130), and the enzyme MxcL, an aldehyde aminotransferase from *Stigmatella aurantiaca* (NCBI Accession No. AAG31130) is added to the host. The R domain and MxcL act to release the terminal intermediate b (FIGS. 26 A & B) or c (FIG. 26 C) from the PKS and aminate it to produce hexane-1,4-diamine.

These approaches should yield the expected even-chain diacid. The PKS genes described herein, or the hosts that carry them, are available from the American Type Culture Collection (ATCC) depository.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A non-naturally occurring hybrid polyketide synthase (PKS) which synthesizes adipic acid, wherein the PKS comprises:
   (a) a first module that is a loading module that incorporates succinyl-CoA, wherein the first module comprises an aspartate-specific adenylation (A) domain from the non-ribosomal peptide synthetase (NRPS) from the calcium-dependent antibiotic (CPA) pathway from *Saccharopolyspora erythraea* linked to a peptidylcarrier protein (PCP) domain from the bleomycin pathway from *Streptomyces verticillus*; wherein the A domain comprises a glutamine substitution for the conserved Asp235 residue of the substrate-binding pocket as defined in the gramicidin S synthase phenylalanine-activating domain; and
   a second module comprising at least one extension module and a TE domain; or
   (b) a first module that is a loading module that incorporates succinyl-CoA, wherein the first module comprises a loading domain and ACP domain of a chondrochloren PKS in which a succinyl-CoA synthetase replaces a CoA ligase domain and
   a second module comprising at least one extension module and a TE domain; or
   (c) an etnangien loading module which incorporates succinate using a trans-AT domain; and
      (i) at least one heterologous extension module, and a TE domain: or
      (ii) extension module 1 from *Sorangium cellulosum* PKS in which DH-ER-KR domains are inserted between the ACP2 and ACP3; and a TE domain; or
      (iii) wherein the etnangien loading module has inactivated the KS domain joined to the KS domain of extension module 2 from *Sorangium cellulosum* PKS linked to a malonyl-specific AT domain joined to DH-ER-KR-ACP-TE domains; or
   (d) a loading module and at least three extension modules as set forth in FIG. 14, wherein the PKS produces the intermediates [a], [b], [c], and [d] set forth in FIG. 14, wherein the 9-carbon backbone of [d] is released from the ACP by the TE domain and converted to adipic and propionic acid by an esterase, an alcohol dehydrogenase, a flavin-binding family monooxygenase, and an aldehyde dehydrogenase as set forth in FIG. 13.

2. The non-naturally occurring hybrid PKS of claim 1, wherein the PKS comprises the modules set forth in (a), wherein the at least one extension module comprises a KS domain joined to an AT-DH-ER-KR-ACP from nystatin module 5 or nystatin module 15 that incorporates malonyl-CoA and fully reduces a corresponding β-carbonyl group; and a TE domain fused to the ACP from the nystatin module 5 or 15.

3. The non-naturally occurring hybrid PKS of claim 2, wherein the KS domain is from the bleomycin pathway from *Streptomyces verticillus* and the TE domain is from the erythromycin pathway.

4. The PKS of claim 2, wherein the A domain is directly linked to the PCP domain.

5. The non-naturally occurring hybrid PKS of claim 1, wherein the PKS comprises the modules set forth in (b) and wherein the at least one extension module comprises a nystatin module 5; and a TE domain.

6. The non-naturally occurring hybrid PKS of claim 1, wherein the PKS comprises the etnangien loading module, the at least one heterologous extension module, and the TE domain as set forth in (c) (i).

7. The non-naturally occurring hybrid PKS of claim 1, wherein the PKS comprises a loading module and three extension modules as set forth in FIG. 14, wherein the PKS produces the intermediates [a], [b], [c], and [d] set forth in FIG. 14, wherein the 9-carbon backbone of [d] is released from the ACP by the TE domain and converted to adipic and propionic acid by an esterase, an alcohol dehydrogenase, a flavin-binding family monooxygenase, and an aldehyde dehydrogenase as set forth in FIG. 13.

8. The non-naturally occurring hybrid PKS of claim 1, wherein the PKS comprises the modules set forth in FIG. 11, and wherein the A domain is a variant of protein DhbE from *Bacillus subtilis*.

9. A recombinant nucleic acid encoding the non-naturally occurring hybrid polyketide synthase (PKS) of claim 1.

10. A replicon comprising the recombinant nucleic acid of claim 9, wherein the replicon is capable of stably maintained in a host cell.

11. The replicon of claim 10, wherein the replicon is a plasmid or vector.

12. The replicon of claim 11, wherein the vector is an expression vector.

13. A host cell comprising the recombinant nucleic acid of claim 9 or the replicon of claim 10.

14. The host cell of claim 13, wherein the host cell when cultured produces adipic acid.

15. A method of producing adipic acid comprising: culturing the host cell of claim 14 in a suitable culture medium such that adipic acid is produced.

16. The method of claim 15, further comprising isolating the adipic acid.

17. The method of claim 16, further comprising reacting the adipic acid with a diamine to produce a nylon.

\* \* \* \* \*